United States Patent [19]

Graeve et al.

[11] Patent Number: 5,232,922
[45] Date of Patent: Aug. 3, 1993

[54] IMIDAZOLE COMPOUNDS, PROCESSES FOR THEIR PREPARATION, PHARMACEUTICALS BASED ON THESE COMPOUNDS AND SOME INTERMEDIATES

[75] Inventors: Rolf Graeve, Taunusstein; Ismahan Okyayuz-Baklouti, Wiesbaden; Dirk Seiffge, Mainz, all of Fed. Rep. of Germany

[73] Assignee: Hoechst Aktiengesellschaft, Frankfurt am Main, Fed. Rep. of Germany

[21] Appl. No.: 652,606

[22] Filed: Feb. 8, 1991

[30] Foreign Application Priority Data

Feb. 10, 1990 [DE] Fed. Rep. of Germany ....... 4004061

[51] Int. Cl.$^5$ ................... A61K 31/535; C07D 413/12
[52] U.S. Cl. .................... 514/235.8; 514/227.8; 514/232.2; 514/252; 514/326; 514/397; 514/398; 544/58.5; 544/139; 544/370; 546/16; 546/210; 548/336; 548/337; 548/341
[58] Field of Search ...................... 544/58.5, 139, 370; 514/227.8, 232.2, 235.8, 252

[56] References Cited

U.S. PATENT DOCUMENTS

| 2,603,649 | 7/1952 | Clapp et al. | 260/309 |
| 3,932,444 | 1/1976 | Ellis | 260/309 |

FOREIGN PATENT DOCUMENTS

| 1222752 | 6/1987 | Canada | 260/249.1 |
| 0095925 | 12/1983 | European Pat. Off. | 403/12 |
| 0096003-A3 | 12/1983 | European Pat. Off. | 403/12 |
| 0249938 | 12/1987 | European Pat. Off. | 417/14 |
| 0284277 | 9/1988 | European Pat. Off. | |
| 0298196 | 1/1989 | European Pat. Off. | 233/90 |

OTHER PUBLICATIONS

L. Harker, Seminars in Thrombosis and Hemostasis, vol. 12, No. 2 (1986), pp. 134–155.
Reuben G. Jones et al., J. of Am. Chem. Soc., vol. 71 (1949), pp. 4000–4002.

*Primary Examiner*—Thurman K. Page
*Assistant Examiner*—Jyothsna Venkat
*Attorney, Agent, or Firm*—Finnegan, Henderson, Farabow, Garrett & Dunner

[57] ABSTRACT

Imidazole compounds of the formula I

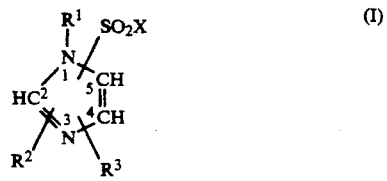

in which
$R^1$ = alkyl,
$R^2$ and $R^3$ = H, halogen or alkyl,
X = OH or an amide radical having certain substituents, processes for their preparation and pharmaceuticals based on these compounds, in particular for the prophylaxis and treatment of circulatory disturbances, especially of disturbances of the microcirculation and of the disorders resulting therefrom, and some novel intermediates for the preparation of the compounds of the formula I, which are 1-methyl-, 1,2-dimethyl- and 1-ethyl-4-imidazolesulfonyl chloride.

11 Claims, No Drawings

IMIDAZOLE COMPOUNDS, PROCESSES FOR THEIR PREPARATION, PHARMACEUTICALS BASED ON THESE COMPOUNDS AND SOME INTERMEDIATES

In recent years, diseases of the circulatory system at over 50% were at the top of all cases of death. Here, in turn, thromboembolic complications mainly dominated. In spite of worldwide intensive efforts to make advances in the elucidation of causes of disease, characterization and recognition of relevant risk factors and development of reliable treatment methods, to this day a satisfactory medicinal treatment is lacking (L. Harker, in: Seminars in Thrombosis and Hemostasis, Vol. 12, No. 2, 134-155, 1986; de Gaetano et al., in: Current issues in thrombosis prevention with antiplatelet drugs, 31, 517-549, 1986). The overriding aim of an antithrombotic, antiischemic treatment is the correction of the disturbed organ functions (for example the muscle power in intermittent claudication) and thus an improvement of the quality of life by prevention of early invalidism and ultimately the prevention of fatal events.

About 5% of all people over 50 years old suffer from peripheral circulatory disturbances, of which easily 10% are in danger of developing critical ischemia of the limbs (CLI=critical limb ischemia). The incidence of CLI is about 500 to 1000 per 1 million people per year. About 60% of these patients receive a vessel replacement, but about 20% suffer the fate of primary amputation. A year later, only about 55% of the patients still possess both lower extremities, but already about 25% have had an amputation and the remaining patients have died. This short account shows in an impressive manner the necessity of an early and effective medicinal treatment of peripheral occlusive diseases.

The previously known imidazolesulfonamides should principally have herbicidal or biocidal properties (cf. CA-A-1,222,752 corresponding to EP-A-96,003; EP-A-95,925, EP-A-0,298,196 and EP-A-249,938), be suitble as textile auxiliaries or plasticizers for plastics (U.S. Pat. No. 3,932,444) or, alternatively, act as carboanhydrase inhibitors (U.S. Pat. No. 2,603,649).

It has now been found that a number of novel imidazole compounds (imidazolesulfonic acids and imidazolesulfonamides) surprisingly have very useful pharmacological properties, in particular those which enable prophylaxis and treatment of circulatory disturbances, especially of disturbances of the microcirculation and the disorders resulting therefrom. They are the compounds of the following formula I; the invention therefore relates to these compounds and their physiologically tolerable salts.

Formula I is

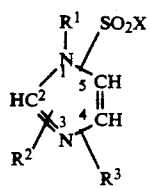

in which
$R^1$ is $(C_1-C_6)$-alkyl,
$R^2$ and $R^3$ are identical or different and in each case are
H,
halogen (F, Cl, Br or I), preferably Cl, or $(C_1-C_3)$-alkyl,
X is OH
or an amino group of the formula II

in which
$R^4$ is H or
$(C_1-C_7)$-, preferably $(C_1-C_4)$-alkyl, optionally substituted by CN, $NH_2$ or COOH,
$R^5$ is a $(C_1-C_8)$-, preferably a $(C_1-C_5)$-alkyl radical, in which—if it has more than 1 carbon atom—there can also be a phenylene radical between 2 carbon atoms and its (aliphatic) carbon atoms are substituted by 1 or more of the following groups:
OH,
$(C_1-C_3)$-alkoxy
phenyl, optionally substituted by 1-3 OH,
$(C_1-C_3)$-alkoxy groups, $(C_1-C_3)$-alkoxy-COOH, and/or
$(C_1-C_3)$-alkoxy-COO$(C_1-C_4)$-alkyl
COOH,
COO$(C_1-C_3)$-alkyl,
$CONH_2$,
CN,
$(C_2-C_5)$-alkynyl,
$NH_2$,

| | |
|---|---|
| $NHR^6$ | in which $R^6$ is identical or different radicals of the type $(C_1-C_4)$-alkyl |
| $N(R^6)_2$ | $(C_2-C_6)$-alkoxyalkyl and |
| $N^{\oplus}(R^6)_3$ | phenylalkyl, having 1-3 carbon atoms in the alkyl moiety, |

$NH-CO-(C_1-C_6)$-alkyl,

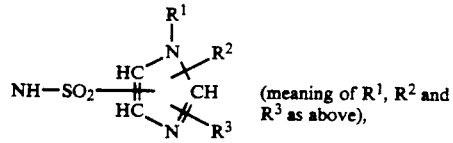

(meaning of $R^1$, $R^2$ and $R^3$ as above), monocyclic 5- to 7-membered saturated or unsaturated—preferably saturated—heterocyclic radicals having 1 nitrogen atom and optionally also an additional nitrogen, oxygen or sulfur atom on the ring, optionally substituted by $(C_1-C_3)$-alkyl,
phenyl,
phenylalkyl having 1-3 carbon atoms in the alkyl moiety,
OH, and/or
oxo (=O), including the open and cyclic ketal forms having 2-6 carbon atoms in the ketal moiety,
and in which the ring sulfur atom—if present—can also be oxidized to the sulfoxide (SO) or sulfone ($SO_2$) form, or in which
$R^4$ and $R^5$, together with the amide nitrogen atom to which they are bonded, form a—preferably saturated—5- to 7-membered heterocyclic ring which, apart from the amide nitrogen, can additionally contain a further heteroatom from the group comprising N, O and S,
where, however, the unsubstituted morpholine ring

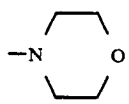

is excluded
and the heterocyclic ring can otherwise be substituted by the following groups:
($C_1$–$C_3$)-alkoxy,
phenylalkyl having 1-4 carbon atoms in the alkyl moiety,
phenyl, optionally substituted by 1 or more—preferably only 1—of the groups:
($C_1$–$C_3$)-alkyl,
OH,
($C_1$–$C_3$)-alkoxy,
($C_1$–$C_3$)-alkoxy-COOH,
($C_1$–$C_3$)-alkoxy-COO($C_1$–$C_4$)alkyl,

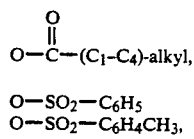

$O-SO_2-C_6H_5$
$O-SO_2-C_6H_4CH_3$,

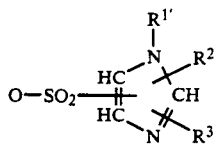

in which $R^{1'}$ has the same meaning as $R^1$ and can additionally also be H, and
$R^2$ and $R^3$ have the abovementioned meaning,
and the ring sulfur atom—if present—can also be oxidized to the sulfoxide (SO) or sulfone ($SO_2$) form.

Preferred compounds of the formula I are those in which at least one of the following features are present:
a) $R^1$ is $CH_3$ or $C_2H_5$,
b) $R^2$ and $R^3$ are identical or different and in each case are H, Cl or $CH_3$ and
c) the —$SO_2X$ radical is situated in the 2- or 4-position of the imidazole ring.

Among the compounds of the formula I, the sulfonamides are furthermore preferred; i.e. the compounds where

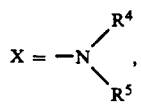  (II)

where the radicals $R^4$ and $R^5$ preferably have the following meaning:
$R^4$ is H and
$R^5$ is a ($C_2$–$C_5$)-alkyl radical in which there is optionally a phenylene radical between 2 carbon atoms and its (aliphatic) carbon atoms are substituted by a total of 1 or 2—preferably only by 1—of the following groups:
hydroxyphenyl $C_6H_4OH$
CN
($C_2$–$C_3$)-alkynyl $NH_2$

| $NHR^6$<br>$N(R^6)_2$ | in which $R^6$ is identical or different radicals of the type ($C_1$–$C_3$)-alkyl, ($C_2$–$C_4$)-alkoxyalkyl and benzyl; |
|---|---| a monocyclic 5- to 6-membered saturated heterocyclic radical from the group comprising:

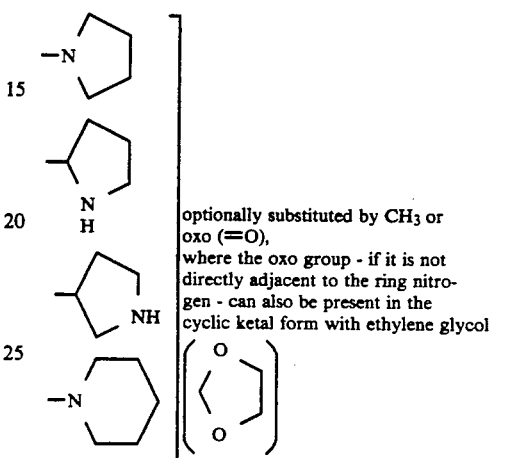

optionally substituted by $CH_3$ or oxo (=O), where the oxo group - if it is not directly adjacent to the ring nitrogen - can also be present in the cyclic ketal form with ethylene glycol

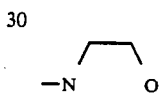

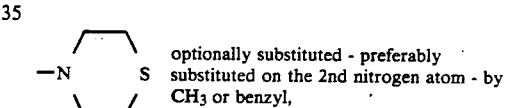

optionally substituted - preferably substituted on the 2nd nitrogen atom - by $CH_3$ or benzyl,

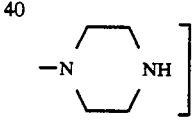

or $R^4$ and $R^5$, together with the amide nitrogen atom to which they are bonded, form a saturated 6-membered heterocyclic ring of the type

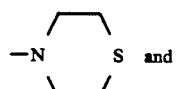 and

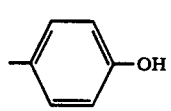 optionally substituted, preferably substituted on the 2nd nitrogen atom - by one of the following radicals:

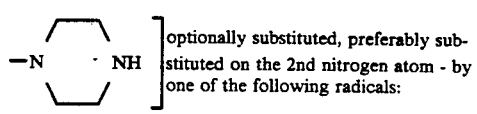

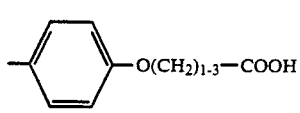

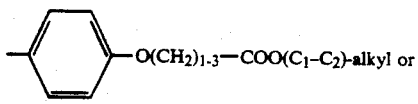

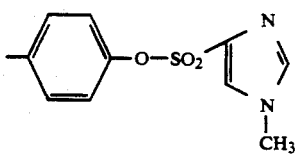

Among the sulfonamides, again those having separate radicals $R^4$ and $R^5$ are somewhat preferred compared to those having—together with the amide nitrogen—$R^4 + R^5$ closed to give a ring.

Particularly preferred compounds of the formula I are

N-(2-morpholinoethyl)-1-methyl-2-imidazolesulfonamide = compound of the formula I in which
$R^1 = CH_3$,
$R^2 = R^3 = H$,
the $SO_2X$ group is in the 2-position and

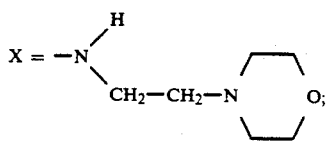

and also

N-(3-morpholinopropyl)-1-methyl-4-imidazolesulfonamide = compound of the formula I in which
$R^1 = CH_3$,
$R^2 = R^3 = H$,
the $SO_2X$ group is in the 4-position and

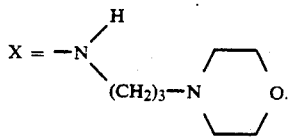

Examples of suitable physiologically tolerable salts are:
—if in the compounds of the formula I acidic groups are present (in particular if X=OH):
Na, K and NH$_4$ salts etc.;
—if in the compounds of the formula I basic groups are present:
hydrochlorides, salts with physiologically tolerable organic acids (acetic acid, maleic acid, fumaric acid etc.), etc.

Some examples of compounds of the formula I according to the invention—both not particularly preferred and preferred—are:
1-methyl-4-imidazolesulfonic acid,
1-ethyl-4-imidazolesulfonic acid,
1-methyl-2-imidazolesulfonic acid,
5-chloro-1-methyl-4-imidazolesulfonic acid,
2-fluoro-1-methyl-4-imidazolesulfonic acid
4-chloro-1-methyl-5-imidazolesulfonic acid,
1-methyl-5-imidazolesulfonic acid,
1,2-dimethyl-5-imidazolesulfonic acid, N-(3-morpholinopropyl)-1-methyl-4-imidazolesulfonamide,
N-(2-morpholinoethyl)-1-methyl-4-imidazolesulfonamide,
N-(4-morpholinobutyl)-1-methyl-4-imidazolesulfonamide,
N-(5-morpholinopentyl)-1-methyl-4-imidazolesulfonamide,
N-(3-morpholino-2-methyl-1-propyl)-1-methyl-4-imidazolesulfonamide,
N-(3-thiomorpholinopropyl)-1-methyl-4-imidazolesulfonamide,
N-butyl-N-(3-morpholino-1-propyl)-1-methyl-4-imidazolesulfonamide,
N-(2-piperidinoethyl)-1-methyl-4-imidazolesulfonamide,
N-[3-(2-methylpiperidino)propyl]-1-methyl-4-imidazolesulfonamide,
N-(5-piperidinopentyl)-1-methyl-4-imidazolesulfonamide,
N-[8-aza-1,4-dioxaspiro(4,5)decyl]-1-methyl-4-imidazolesulfonamide,
N-(2-pyrrolidinoethyl)-1-methyl-4-imidazolesulfonamide,
N-[2-(1-methyl-2-pyrrolidinyl)-ethyl]-1-methyl-4-imidazolesulfonamide,
N-<3[bis(2-methoxyethyl)amino]propyl>-4-imidazolesulfonamide,
N-[4-(4-hydroxyphenyl)piperazino]-1-methyl-4-imidazolesulfonamide,
N-[3-(4-benzyl-1-piperazinyl)propyl]-1-methyl-4-imidazolesulfonamide,
N-[3-(4-methylpiperazino)propyl]-1-methyl-4-imidazolesulfonamide,
N-[3-(N-benzyl-N-methylamino)-1-propyl]-1-methyl-4-imidazolesulfonamide,
N-(3-morpholinopropyl)-1-methyl-2-imidazolesulfonamide,
N-(2-morpholinoethyl)-1-methyl-2-imidazolesulfonamide,
N-(3-morpholinopropyl)-4-chloro-1-methyl-5-imidazolesulfonamide,
N-(3-mprholinopropyl)-5-chloro-1-methyl-4-imidazolesulfonamide,
N-(3-morpholinopropyl)-1,2-dimethyl-4-imidazolesulfonamide,
N-(5-morpholino-1-pentyl)-5-chloro-1-methyl-4-imidazolesulfonamide,
N-(3-morpholinopropyl)-1-propyl-4-imidazolesulfonamide,
N-(3-morpholinopropyl)-1-propyl-5-imidazolesulfonamide,
N-(3-morpholinopropyl)-1-n-butyl-4-imidazolesulfonamide,
N-(3-morpholinopropyl)-1-n-butyl-5-imidazolesulfonamide,
N-(3-morpholinopropyl)-1-ethyl-4-imidazolesulfonamide,
N-(1,3-dimorpholino-2-propyl)-1-methyl-4-imidazolesulfonamide,
N-[4-(4-hydroxyphenyl)piperazino]-5-chloro-1-methyl-4-imidazolesulfonamide,
1-(1-methyl-5-chloro-4-imidazolesulfonyl)-4-[4-(1-methyl-5-chloro-4-imidazolesulfonyloxy)phenyl]piperazine,
4-(1-methyl-4-imidazolesulfonyl)tetrahydro-4H-1,4-thiazine 1-[3-(1-methyl-5-imidazolesulfonyl)aminopropyl]-2-pyrrolidinone,
N-(3-methoxypropyl)-1-methyl-4-imidazolesulfonamide,
N-(4-hydroxyphenethyl)-1-methyl-4-imidazolesulfonamide,
N-(4-hydroxyphenethyl)-5-chloro-1-methyl-4-imidazolesulfonamide,
1,6-bis(5-chloro-1-methyl-4-imidazolesulfonamido)hexane,
N-(2-cyanoethyl)-1-methyl-4-imidazolesulfonamide,
N-(5-cyanopentyl)-1-methyl-4-imidazolesulfonamide,
N-(3-propargyl)-1-methyl-4-imidazolesulfonamide,
4-[2-(1-methyl-4-imidazolesulfonyl)aminoethyl]phenoxyacetic acid,
4-[2-(5-chloro-1-methyl-4-imidazolesulfonyl)aminoethyl]phenoxyacetic acid,
N-(3-morpholino-1-propyl)-1-methyl-5-imidazolesulfonamide,
1,6-bis(1-methyl-4-imidazolesulfonamido)hexane,
N-[3-(1-piperazinyl)propyl]-1-methyl-4-imidazolesulfonamide,
4-methyl-4-[3-(1-methyl-4-imidazolesulfamoyl)-1-propyl]morpholinium iodide,
4-(1-methyl-4-imidazolesulfonyl)tetrahydro-4H-1,4-thiazine-1,1-dioxide,
Ethyl 4-[4-(5-chloro-1-methyl-4-imidazolesulfonyl)piperazin-1-yl]phenoxyacetate
N-(6-aminohexyl)-1-methyl-4-imidazolesulfonamide,
N-(3-aminopropyl)-1-methyl-4-imidazolesulfonamide,
N-(3-thiomorpholinopropyl)-1-methyl-4-imidazolesulfonamide-S-oxide,
N-(3-methylamino-1-propyl)-1-methyl-4-imidazolesulfonamide,
N-[4-(morpholinomethyl)benzyl]-1-methyl-4-imidazolesulfonamide,
N-(3-dibenzylaminopropyl)-1-methyl-4-imidazolesulfonamide,
N-(3-dimethylaminopropyl)-1-methyl-4-imidazolesulfonamide,
N-(3-N-ethyl-N-isopropylaminopropyl)-1-methyl-4-imidazolesulfonamide,
N-[bis(2-cyanoethyl)]-1-methyl-4-imidazolesulfonamide,
N-[2-(2-pyridyl)ethyl]-1-methyl-4-imidazolesulfonamide,
N-(5-carboxypentyl)-1-methyl-4-imidazolesulfonamide and
N-(5-acetylpentyl)-1-methyl-4-imidazolesulfonamide.

The compounds of the formula I and their physiologically tolerable salts are prepared according to the invention by a) converting an imidazole derivative of the general formula III

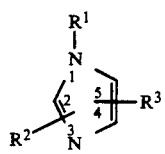

in which $R^1$, $R^2$ and $R^3$ have the meaning mentioned in formula I, and one of the positions 4 or 5 is unsubstituted, by sulfonation by means of sulfuric acid or oleum, preferably at temperatures of about 150°–180° C., into the compounds of the formula Ia according to the invention

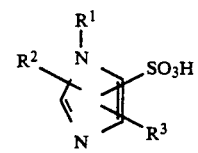

in which $R^1$, $R^2$ and $R^3$ likewise have the meaning mentioned in formula I, or by b) converting an imidazole derivative of the general formula IV,

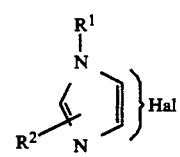

in which $R^1$ and $R^2$ have the meaning mentioned in formula I, one of the positions 4 or 5 carries a halogen atom (Cl, Br or I) and the other is unsubstituted, by sulfonation and subsequent hydrogenolytic dehalogenation by means of noble metal catalysts, preferably at hydrogen pressures of about 1–5 bar in polar solvents such as alcohol and/or water and room temperature to about 60° C., into a compound of the formula Ib

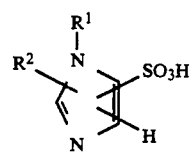

(meaning of $R^1$ and $R^2$ as in formula I)
—the temporary protection of the 4- or 5-position in this case thus prevents the sulfonation in this position and therefore leads to uniform products—or by c) hydrolyzing an imidazole derivative of the general formula V,

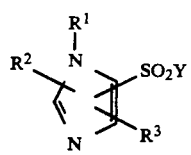

in which $R^1$, $R^2$ and $R^3$ have the meaning mentioned in formula I and Y is halogen, preferably chlorine, to give the sulfonic acids of the formula Ia according to the invention with the meanings for $R^1$, $R^2$ and $R^3$ mentioned there—preferably by means of water at room temperature, or by d) oxidizing an imidazole derivative of the general formula VI or VI'

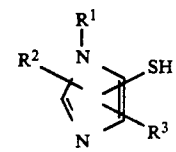

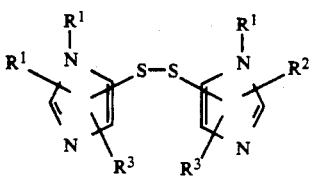

in which $R^1$, $R^2$ and $R^3$ have the meaning mentioned in formula I, to give the corresponding imidazolesulfonic acid (formula Ia), preferably by oxidizing by the process according to EP-A-95,925 with chlorine to give an intermediate imidazolesulfonyl chloride and then directly hydrolyzing in aqueous medium, or by e) reacting an imidazolesulfonyl halide of the general formula V (see variant c) with an amine of the formula H-II

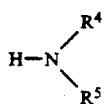

in which $R^4$ and $R^5$ have the same meaning as in formula II, to give the sulfonamides of the formula Ic according to the invention

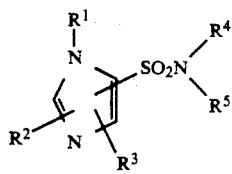

in which $R^1$ to $R^5$ have the meanings mentioned in the formulae I and II.

On the one hand, this reaction can be carried out in the absence of additional acid scavengers, the corresponding hydrochlorides being formed in the conversion of di- and polyamines, which can either be isolated as such or converted into the free bases, which in turn can either be isolated as such or converted into other salts, for example those of fumaric acid.

On the other hand, the reaction can also be carried out in the presence of acid scavengers, for example an excess of the amine $H-N(R^4)R^5$ to be reacted (formula H-II), a lower tertiary amine such as triethylamine, or inorganic basis such as potassium carbonate.

The sulfonamide formation can be carried out in an anhydrous solvent which is inert to the reaction components, preferably acetonitrile or dichloromethane, in a suitable procedure, but also in protic solvents, for example water or phenol in each case at temperatures between about $-30°$ C. and the boiling temperatures of the solvent used, but preferably between about $0°$ C. and $30°$ C.

The amines of the formula H-II used as starting materials in these process variants are for the most part known or can be prepared by methods which are known from the literature, predominantly by hydrogenation or reduction of appropriately substituted nitriles. In cases in which hydrogenation is not applicable, resort can be made, for example, to the phthalimide method. Thus, as an example it may be mentioned that N-(3-bromopropyl)phthalimide reacts with thiomorpholine to give N-(3-thiomorpholinopropyl)phthalimide, which can be converted by hydrazine and subsequent action of hydrochloric acid into the hydrochloride of N-(3-aminopropyl)thiomorpholine.

The compounds of the formula I and their physiologically tolerable salts are furthermore prepared according to the invention by f) reacting imidazole derivatives of the general formula VII,

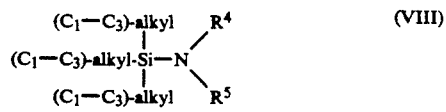

in which $R^1$ and $R^2$ have the meaning indicated in formula I and Y is identical or different halogen atoms (Cl, Br or I), with amines of the formula H-II and then subjecting the products to hydrogenolytic dehalogenation, preferably over noble metal catalysts, such as palladium on carbon, in order to obtain the sulfonamides unsubstituted in the 4- or 5-position of the formula Id

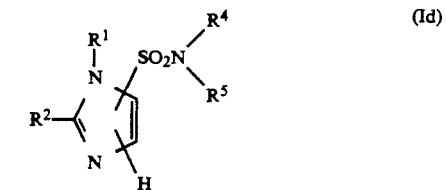

(meaning of $R^1$, $R^2$, $R^4$ and $R^5$ as in formulae I and II), or by g) reacting an imidazolesulfonyl halide of the general formula V (see variant c) with a trialkylsilylamine of the formula VIII

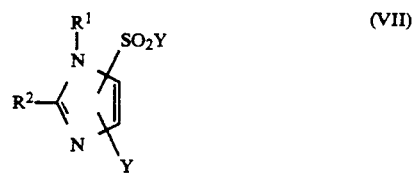

where $R^4$ and $R^5$ have the meaning mentioned in formula II and a preferred $C_1-C_3$-alkyl radical is the methyl radical, in order to obtain the sulfonamides of the formula Ic according to the invention (see variant e).

The silylated amines can be used either as pure compounds or as crude products prepared freshly—for example by means of MSTFA (N-methyl-N-trimethylsilyltrifluoroacetamide). The reaction with the respective imidazolesulfonyl halide V is usually carried out in inert solvents, such as dichloromethane or acetonitrile, at temperatures between about $-30°$ to about $120°$ C., preferably between about $-30°$ C. and the boiling point of the solvent. This process directly yields the free base and is additionally indicated in the case of less reactive and sensitive compounds.

h) Compounds according to the invention as in formula I (where $X=-N(R^4)R^5$, where $R^4$ carries at least one $NH_2$ group and/or $R^5$ carries at least one primary or secondary amino group) and their physiologically tolerable salts can additionally be prepared by reacting amines of the formula H—N(R$^4$)R$^5$, which on their radicals R$^4$ and/or R$^5$ carry at least one N-protected—preferably N-benzylated—appropriate amino group, with the imidazolesulfonyl halides of the formula V (see variant c), as described under e), and subsequently setting the resulting sulfonamides free from the protecting group(s), in the case of the N-benzyl protective group preferably by hydrogenolysis at low hydrogen pressures (about 1–5 bar), slightly elevated temperatures (room temperature to about 60° C.) and in ethanolic-aqueous ammonia solution over noble metal catalysts, such as palladium on carbon.

From the number of protecting groups which are suitable for the protection of the second amino group from attack by an imidazolesulfonyl halide and can be removed again, the following—apart from the preferred benzyl group already mentioned—may additionally be emphasized: triphenylmethyl, trifluoroacetyl, benzyloxycarbonyl, tert.-butyloxycarbonyl, phthalyl, formyl and acetyl.

i) Those imidazole derivatives of the formula I where X=—N(R$^4$)R$^5$, where at least one of the radicals R$^4$ and R$^5$ carries one or more primary amino groups, can furthermore be prepared by reacting imidazolesulfonyl halides of the formula V (see variant c) with appropriate aminonitriles analogously to the procedure as in varient e) and reducing the imidazolesulfonylaminonitriles thus obtained to the corresponding amino compounds, preferably by catalytic hydrogenation using noble metal catalysts such as palladium on carbon in alcoholic-ammoniacal solution at elevated hydrogen pressure (about 2–5 bar) at room temperature to slightly elevated temperature (up to about 60° C.).

j) Imidazole derivatives of the formula I where X=—N(R$^4$)R$^5$, where R$^5$ is the carrier of a quaternary amino group —N$^\oplus$(R$^6$)$_3$, in which the radicals R$^6$ can be identical or different, can additionally be prepared as follows:

The compounds of the formula I with tertiary amino groups —N(R$^6$)$_2$ as a substituent of R$^5$ are quaternized by means of an alkylating agent such as an alkyl halide, preferably iodomethane, a sulfuric acid ester, preferably dimethyl sulfate or an arylsulfonic acid ester, preferably methyl p-toluenesulfonate, in solvents such as nitromethane, acetonitrile, alcohols or aqueous-alcoholic solutions, preferably in the range from room temperature up to the boiling temperature of the solvent.

k) Other substances according to the invention can be prepared by oxidizing imidazole derivatives of the general formula I where X=—N(R$^4$)R$^5$, where R$^5$, or R$^4$ and R$^5$ are together a carrier of at least one sulfide group, preferably in the form of a thiomorpholine ring, to the corresponding sulfoxides or sulfones. Suitable oxidants for this are sodium iodate in aqueous-methanolic solution or peroxides such as m-chloroperoxybenzoic acid, peracetic acid or hydrogen peroxide in solvents such as chloroform or acetic acid or water.

l) Among the compounds of the formula I, some can be synthesized by alkylating imidazole derivatives of the general formula I where X=—N(R$^4$)R$^5$, where R$^5$ or R$^4$ and R$^5$ together carry at least one aryl radical, which is substituted by one or more phenolic hydroxyl groups, with alkylating reagents, preferably ω-halo-fatty acid derivatives, to the corresponding phenol ethers in the presence of basic compounds, such as sodium hydroxide, in a polar solvent, such as ethanol, in the temperature range from about 0° C. up to the boiling point of the solvent.

If the products are derivatives of the ω-fatty acid esters, these can furthermore also be subjected to acidic or alkaline hydrolysis under standard conditions or aminolysis using ammonia solutions or solutions of lower primary or secondary amines, preferably methylamine, in order to give the corresponding carboxylic acids or carboxamides.

m) These phenolic imidazole derivatives mentioned under l) can also be reacted with acylating agents such as alkylcarbonyl chlorides, preferably those of acetic, propionic or butyric acid, with arylsulfonyl chlorides, preferably benzene- or toluenesulfonyl chloride, and with imidazolesulfonyl halides of the general formula V (see variant c), in which R$^1$ can additionally still be hydrogen, to give the corresponding phenol esters. In this case, basic anhydrous conditions are expedient.

The compounds of the formula I and their physiologically tolerable salts are very highly suitable as a result of their useful pharmacological properties for use as medicines.

The invention therefore also relates to medicaments containing at least one compound of the formula I and/or at least one of its physiologically tolerable salts. The medicaments are preferably suited to the prophylaxis and/or treatment of circulatory disturbances, in particular of disturbances of the microcirculation and the disorders resulting therefrom.

The disorders resulting from circulatory disturbances, in particular from disturbances of the microcirculation, are principally ischemic skeletal and/or cardiac muscle disorders, in particular intermittent claudication, ulcer of the leg and degenerative and/or inflammatory muscle disorders of various geneses with or without muscle atrophy, vasculitis with thrombotic events, arterial and venous blood clots (for example thromboses, shock).

Because of the circulation-promoting action of the compounds and medicaments according to the invention, in particular in the micro region, the compounds and medicaments are also active in arteriosclerosis, in surgical aftertreatment for the prevention of postoperative thromboses, for the aftertreatment of cancer to prevent or reduce formation of metastases, in the treatment of patients who are attached to heat-lung machines or renal dialysis and, finally, also of patients after stroke or myocardial infarct and also for healing of wounds after traumas and exogenic noxae.

The medicaments according to the invention are in general administered orally or parenterally, but rectal administration is in principle also possible. Suitable solid or liquid pharmaceutical preparations are, for example, granules, powders, tablets, coated tablets (micro)capsules, suppositories, syrups, emulsions, suspensions, aerosols, drops or injectable solutions in ampoule form and preparations having sustained release of active compound, in whose preparation excipients and additives and/or auxiliaries such as disintegrants, binders, coating agents, swelling agents, glidants or lubricants, flavorings, sweeteners or solubilizers are customarily used. Examples of frequently used excipients or auxiliaries are magnesium carbonate, titanium dioxide, lactose, mannitol and other sugars, talc, lactoprotein, gelatin, starch, vitamins, cellulose and its derivatives, animal and vegetable oils, polyethylene glycols and solvents, such as, for example, sterile water, alcohols, glycerol and polyhydric alcohols.

The pharmaceutical preparations are preferably prepared and administered in dosage units, each unit containing a certain dose of at least one compound of the formula I and/or at least one corresponding physiologically tolerable salt as the active constituent. In the case of solid dosage units such as tablets, capsules and suppositories, this dose can be up to about 500 mg, but preferably about 50 to 300 mg, and in the case of injection solutions in ampoule form up to about 150 mg, but preferably about 10 to 100 mg. Only small differences exist between the doses of the compounds of the formula I and of their salts.

For the treatment of an adult patient—depending on the activity of the compounds according to formula I in humans—daily doses of about 20 to 500 mg of active compound, preferably about 50 to 300 mg, are indicated on oral administration and of about 5 to 300 mg, preferably about 10 to 100 mg, on intravenous administration. Under certain circumstances, however, higher or lower daily doses may also be appropriate. The administration of the daily dose can be carried out either by single administration in the form of an individual dosage unit or else several smaller dosage units or by multiple administration of subdivided doses at specific intervals.

The medicaments according to the invention are produced by bringing at least one compound of the formula I and/or at least one of its physiologically tolerable salts into the or a form suitable for administration using customary excipients and, if appropriate, additives and/or auxiliaries.

For the production of the abovementioned pharmaceutical preparation forms, the medicaments according to the invention can also be formulated together with other suitable active compounds, for example antithrombotics, antihyperlipidemics, analgesics, sedatives, antidepressives, antianginal agents, cardiotonics, antiarrhythmics, diuretics, antihypertensives including $\beta$-receptor and calcium blockers, plasma expanders and other vasotherapeutics.

Finally, some precursors or intermediates for the preparation of the compounds of the formula I are also novel and therefore likewise a subject of the invention; they are the compounds
1-methyl-,
1,2-dimethyl- and
1-ethyl-4-imidazolesulfonyl chloride.

These compounds are advantageously prepared by a) reacting 1-methyl- or 1,2-dimethyl- or 1-ethylimidazole with chlorosulfonic acid $ClSO_3H$, optionally with subsequent addition of $SOCl_2$, or by b) oxidatively chlorinating 1-methyl- or 1,2-dimethyl- or 1-ethyl-4-mercaptoimidazole with $Cl_2$.

A more detailed explanation of the two process variants:

a) The reaction with chlorosulfonic acid is expediently carried out at elevated temperature, preferably between about 130° C. and 160° C., if possible without aspirating the resulting hydrogen chloride.

For better reaction control, the possible subsequent addition of thionyl chloride is carried out at slightly elevated temperatures, preferably between about 60° and 80° C., at which the reaction mixture has become easily stirrable and rapid reaction of the thionyl chloride is ensured.

By pouring the reaction mixture into an ice-water mixture, these imidazole derivatives can be precipitated as almost pure 1-alkyl-4-imidazolesulfonyl chlorides, while resulting 5-imidazolesulfonyl chlorides mainly remain in solution and can be hydrolyzed to sulfonic acids. To avoid losses by hydrolysis of the 4-imidazolesulfonyl chlorides also, rapid drying is recommended, preferably in solvents such as dichloromethane, using drying agents such as sodium sulfate.

b) 2-mercaptoimidazoles can be oxidized with chlorine, if possible used stoichiometrically, to give the 2-imidazolesulfonyl chlorides by methods known from the literature [R. G. Jones et al., J. Am. Chem. Soc. 71, 4000 (1949)]. The conditions for the chlorine-oxidation of the 1-alkyl- and 1,2-dialkyl-4-mercaptoimidazoles are similar (at about $-10°$ to $+10°$ C. in dilute hydrochloric acid).

The following (preparation) examples are intended to serve to explain the invention in more detail.

The structures of all compounds described below were confirmed by elemental analysis and IR and $^1$H-NMR spectra. In the following, in vacuo is understood as meaning that of the water-jet pump. Silica gel plates (special 0.25 mm silica gel 60$F_{254}$, Riedel-de-Haen AG, D-3016 Seelze) were used for thin-layer chromatography.

The yields indicated are not optimized.

After the preparation examples, a pharmacological section then additionally follows, from which the activity of the compounds according to the invention is clear; the pharmacological section also contains comparison values compared with the standard therapeutic pentoxifylline (=1-(5-oxohexyl)-3,7-dimethylxanthine).

(PREPARATION) EXAMPLES

A) Compounds of the formula I where X=OH

Example 1

5-Chloro-1-methyl-4-imidazolesulfonic acid 33 g (0.28 mol) of 5-chloro-1-methylimidazole in 200 ml of fuming sulfuric acid are heated at 160°-180° C. for 4 hours. After cooling, the reaction mixture is cautiously added to ice. The product crystallizes out from the cold aqueous solution (about 1.5 l). After recrystallizing twice from water, the title compound is obtained in the form of coarse yellowish crystals of melting point 309°-310° C.

Yield: 34 g (46.9% of theory).

Example 2

1-Ethyl-4-imidazolesulfonic acid 5.6 g (29 mmol) of 1-ethyl-4-imidazolesulfonyl chloride from Example C-2 are suspended in 70 ml of water at room temperature until a clear solution is formed. After evaporating in vacuo, the residue is recrystallized from ethanol/water in order to give the title compound of melting point 278° C.

Yield: 5 g (99% of theory).

Example 3

1-Methyl-4-imidazolesulfonic acid

In an analogous manner to that described in Example 2, the title compound of melting point 288°-289° C., after recrystallizing from ethanol/methanol, is obtained from 1-methyl-4-imidazolesulfonyl chloride from Example C-1 in about 70% yield.

Example 4

1-Methyl-2-imidazolesulfonic acid

In an analogous manner to that described in Example 2, the title compound of melting point 234°–236° C., after recrystallization from ethanol/methanol, is obtained from 1-methyl-2-imidazolesulfonyl chloride [R. O. Roblin, jr. and J. W. Clapp, J. Am. Chem. Soc. 72, 4890 (1950)] in about 72% yield.

Example 5

4-Chloro-1-methyl-5-imidazolesulfonic acid

In an analogous manner to that described in Example 2, the title compound of melting point 260°–261° C. is obtained from 4-chloro-1-methyl-5-imidazolesulfonyl chloride [M. H. Fisher, W. H. Nicholson and R. S. Stuart, Can. J. Chem. 39, 1336 (1961)] in about 39% yield.

Example 6

1-Methyl-5-imidazolesulfonic acid

A solution of 3.1 g (17 mmol) of 1-methyl-4-chloro-5-imidazolesulfonic acid from Example 5 in 100 ml of water is hydrogenated to constant pressure at 25° C. in the presence of 0.5 g of Pd/C catalyst with shaking at an initial pressure of 3.45 bar of hydrogen. The crystalline residue remaining after filtering off the catalyst and evaporating the water in vacuo is recrystallized from ethanol in order to give the title compound of melting point 286°–287° C.

Yield: 1.5 g (58.5% of theory).

B) Compounds of the formula I where X=

Example 7

N-(3-Morpholinopropyl)-1-methyl-4-imidazolesulfonamide (hydrochloride)

A solution of 30 g (0.17 mol) of 1-methylimidazole-4-sulfonyl chloride from Example C-1 in 150 ml of acetonitrile is added dropwise to a solution of 24 ml (0.17 mol) of 3-morpholinopropylamine in 50 ml of acetonitrile (or dichloromethane). The temperature of the reaction mixture is kept at room temperature or below by external cooling with ice-water. Stirring is continued for 6 h at room temperature. The precipitate deposited is filtered off with suction and recrystallized from acetonitrile in order to give 46 g (85% of theory) of the title compound (hydrochloride) of melting point 207°–208° C.

To form the free base, the hydrochloride is suspended in dichloromethane and shaken with the equivalent amount of a 1H $K_2CO_3$ solution. The residue remaining after separating off the aqueous phase, drying and removing the solvent in vacuo is recrystallized from acetonitrile. The free base then has a melting point of 138°–139° C.

Example 8

N-(3-Morpholinopropyl)-1-methyl-4-imidazolesulfonamide 16.7 g (46.5 mmol) of 5-chloro-N-(3-morpholino-1-propyl)-1-methyl-4-imidazolesulfonamide hydrochloride from Example 32 are hydrogenated at 25° C. and 3.45 bar in the presence of 3 g of Pd/C catalyst in 250 ml of water. The residue remaining after filtration and evaporation in vacuo is converted into the free base using saturated potassium carbonate solution, extracted with dichloromethane and recrystallized from dioxane/diisopropyl ether in order to give the crystalline title compound, identical with that as in Example 7.

Yield: 6.3 g (43% of theory).

The respective title compound of lines a is obtained from 1-methyl-4-imidazolesulfonyl chloride and the amine of lines b in an analogous manner to that in Example 7:

| Ex. | Name | Melting point °C. (solvent for recrystallization) |
| --- | --- | --- |
| 9 a: | N-(2-morpholinoethyl)-1-methyl-4-imidazolesulfonamide | 142–143 (EtOH) |
| b: | 2-morpholinoethylamine | |
| 10 a: | N-(4-morpholinobutyl)-1-methyl-4-imidazolesulfonamide hydrochloride | 175–176 ($CH_3CN$) |
| b: | 4-morpholinobutylamine | |
| 11 a: | N-(5-morpholinopentyl)-1-methyl-4-imidazolesulfonamide hydrochloride | 195–196 (EtOH) |
| b: | 5-morpholinopentylamine | |
| 12 a: | N-(3-morpholino-2-methyl-1-propyl)-1-methyl-4-imidazolesulfonamide hydrochloride | 164–165 (EtOH) |
| b: | 3-morpholino-2-methyl-1-propylamine | |
| 13 a: | N-(3-thiomorpholinopropyl)-1-methyl-4-imidazolesulfonamide hydrochloride | 224 (EtOH/MeOH) |
| b: | 3-thiomorpholinopropylamine = N-(3-aminopropyl)thiomorpholine | |

Preparation of this starting product:
18 g (67 mmol) of N-(3-bromopropylphthalimide), 6.9 g (67 mmol) of thiomorpholine and 6.8 g (68 mmol) of triethylamine are dissolved in 150 ml of absolute chloroform and heated to reflux under argon for 3 hours. After concentrating in vacuo, the residue is taken up with isopropanol. The precipitate deposited on cooling in the ice bath is filtered off. Water is added to the filtrate and it is adjusted to pH 4–5 using 4 N hydrochloric acid. After extracting this solution by shaking dichloromethane, the aqueous phase is neutralized using sodium bicarbonate and concentrated in vacuo. The thin layer chromatographically uniform residue remaining, crude N-(3-thiomorpholinopropyl)phthalimide, is directly subjected to hydrazinolysis. For this, 14 g (48 mmol) of this crude product are dissolved in 70 ml of absolute ethanol and 3 g (48 mmol) of 80% strength hydrazine hydrate are added dropwise at 70° C., whereupon a precipitate (phthalazine) soon deposits. After 3 hours' reflux, a further 0.5 g (8 mmol) of hydrazine hydrate is added to complete the reaction and the mixture is held at reflux for a further 2 hours. The reaction mixture is then adjusted to about pH 1 using 5 ml of water and 10 ml of concentrated hydrochloric acid. After heating to reflux for 1 hour, the precipitate deposited is filtered

-continued

| Ex. | Name | Melting point °C. (solvent for recrystallization) |
|---|---|---|
| | off and washed with water. The filtrate is neutralized and evaporated to dryness in vacuo. The salts deposited after addition of ethanol are filtered off with suction. The filtrate is evaporated in vacuo and the residue (9 g) is subjected to bulb tube distillation. The title compound passes over at 0.1 torr at an air bath temperature of 180° C. as a colorless oil. Yield: 2 g (20% of theory) | |
| 14 a: | N-[4-(morpholinomethyl)benzyl]-1-methyl-4-imidazolesulfonamide hydrochloride | 272-273 (EtOH/ MeOH) |
| b: | 4-(morpholinomethyl)benzylamine | |
| 15 a: | N-butyl-N-(3-morpholino-1-propyl)-1-methyl-4-imidazolesulfonamide hydrochloride | 176 (CH$_2$CN) |
| b: | N-butyl-N-(3-morpholino-1-propyl)-amine | |
| 16 a: | N-(2-piperidinoethyl)-1-methyl-4-imidazolesulfonamide hydrochloride | 188-189 (CH$_3$CN) |
| b: | 2-piperidinoethylamine | |
| 17 a: | N-[3-(2-methylpiperidino)-propyl]-1-methyl-4-imidazolesulfonamide hydrochloride | 186-187 (CH$_3$CN) |
| b: | 3-(2-methylpiperidino)propylamine | |
| 18 a: | N-(5-piperidinopentyl)-1-methyl-4-imidazolesulfonamide hydrochloride | 180-181 (i-PrOH) |
| b: | 5-piperidinopentylamine | |
| 19 a: | N-[8-aza-1,4-dioxaspiro-(4,5)decyl]-1-methyl-4-imidazolesulfonamide hydrochloride | 164-165 (i-PrOH/ EtOH) |
| b: | 8-aza-1,4-dioxaspiro-(4,5)-decylamine | |
| 20 a: | N-(2-pyrrolidinoethyl)-1-methyl-4-imidazolesulfonamide hydrochloride | 149-150 (EtOH) |
| b: | 2-pyrrolidinoethylamine | |
| 21 a: | N-[2-(1-methyl-2-pyrrolidinyl)-ethyl]-1-methyl-4-imidazolesulfonamide hydrochloride | 163-164 (EtOH/ i-PrOH) |
| b: | 2-(1-methyl-2-pyrrolidinyl)-1-ethylamine | |
| 22 a: | N-(3-dimethylaminopropyl)-1-methyl-4-imidazolesulfonamide hydrochloride | 190-191 (EtOH/ i-PrOH) |
| b: | 3-dimethylaminopropylamine | |
| 23 a: | N-<3-[bis(2-methoxyethyl)-amino]-propyl>-4-imidazolesulfonamide | oil |
| b: | 3-[bis(2-methoxyethyl)amino]propylamine | |
| 24 a: | N-(3-dibenzylaminopropyl)-1-methyl-4-imidazolesulfonamide | 123-124 (EtOH/ i-PrOH) |
| b: | dibenzylaminopropylamine | |
| 25 a: | N-[4-(4-hydroxyphenyl)-piperazino]-1-methyl-4-imidazolesulfonamide | 259-260 (EtOH/ H$_2$O) |
| b: | 4-(4-hydroxyphenyl)piperazine | |
| 26 a: | N-[3-(4-benzyl-1-piperazinyl)-propyl]-1-methyl-4-imidazolesulfonamide hydrochloride | 179-180 (EtOH) |
| b: | 3-(4-benzyl-1-piperazinyl)propylamine | |

Example 27

N-[3-(4-Methylpiperazino)propyl]-1-methyl-4-imidazolesulfonamide dihydrogenfumarate In an analgous manner to that described in Example 7, the free base of the title compound is obtained from 1-methyl-4-imidazolesulfonyl chloride and 3-(4-methylpiperazino)propylamine. The dihydrogenfumarate crystallizing in about 42% yield after addition of twice the molar amount of ethanolic fumaric acid melts at 209°-210° C.

Example 28

N-[3-(N-Benzyl-N-methylamino)-1-propyl]-1-methyl-4-imidazolesulfonamide hydrogenfumarate In an analogous manner to that described in Example 7, the free base of the title compound is obtained from 1-methyl-4-imidazolesulfonyl chloride and 3-(N-benzyl-N-methylamino)-1-propylamine. The hydrogenfumarate crystallizing after addition of an equimolar amount of ethanolic fumaric acid melts at 184°-185° C.

Yield: 53.4% of theory.

The following are obtained in an analogous manner to that described in Example 7

29) N-(3-Morpholinopropyl)-1-methyl-2-imidazolesulfonamide hydrochloride, melting point 177°-178° C. (from ethanol) from 1-methyl-2-imidazolesulfonyl chloride and 3-morpholinopropylamine.

30) N-(2-Morpholinoethyl)-1-methyl-2-imidazolesulfonamide hydrochloride, melting point 197°-198° C. (from ethanol) from 1-methyl-2-imidazolesulfonyl chloride and 2-morpholinoethylamine.

31) N-(3-Morpholinopropyl)-4-chloro-1-methyl-5-imidazolesulfonamide, melting point 113°-114° C. (from ethanol) from 4-chloro-1-methyl-5-imidazolesulfonyl chloride and 3-morpholinopropylamine.

32) N-(3-Morpholinopropyl)-5-chloro-1-methyl-4-imidazolesulfonamide hydrochloride, melting point 179°-180° C. (from methanol/isopropanol) from 5-chloro-1-methyl-4-imidazolesulfonyl chloride and 3-morpholinopropylamine.

33) N-(3-Morpholinopropyl)-1,2-dimethyl-4-imidazolesulfonamide hydrochloride, melting point 181°-182° C. (from ethanol) from 1,2-dimethyl-4-imidazolesulfonyl chloride and 3-morpholinopropylamine.

34) N-(5-Morpholino-1-pentyl)-5-chloro-1-methyl-4-imidazolesulfonamide hydrochloride, melting point 218°-219° C. (from ethanol) from 5-chloro-1-methyl-4-imidazolesulfonyl chloride and 5-morpholinopentylamine.

35) N-(3-Morpholinopropyl)-1-propyl-4-imidazolesulfonamide and N-(3-morpholinopropyl)-1-propyl-5-imidazolesulfonamide as a 4,5-position isomer mixture to be obtained from the isomer mixture of 1-propyl-4-and 1-propyl-5-imidazolesulfonyl chloride from Example C-4 and N-(3-aminopropyl)morpholine in the ratio 20.4%:79.5%. This mixture can be eluted separately by means of a mixture of water:acetic acid:acetonitrile (7.5:1.5:1) b, HPLC on modified silica gel (RP 18, Merck).

36) N-(3-Morpholinopropyl)-1-n-butyl-4-imidazolesulfonamide and N-(3-morpholinopropyl)-1-n-butyl-5-imidazolesulfonamide is to be obtained as a 4,5-position isomer mixture from the isomer mixture of 1-butyl-4- and 1-butyl-5-imidazolesulfonyl chlorides from Example C-5 and N-(3-aminopropyl)morpholine in the ratio 68.1%:17.5%. This mixture can be eluted separately by means of a mixture of water:acetic acid:acetonitrile (7.5:1.5:1) by HPLC on modified silica gel (RP 18, Merck).

Example 37

N-(3-Morpholinopropyl)-1-ethyl-4-imidazolesulfonamide hydrogenfumarate

Analogously to Example 7, 10 g (51 mmol) of 1-ethyl-4-imidazolesulfonyl chloride from Example C-2 are reacted with 7.5 ml (51 mmol) of 3-morpholinopropylamine in 200 ml of acetonitrile and the mixture is correspondingly worked up. The hydrochloride thus obtained is dissolved in methanol and converted into the free base by means of an equivalent amount of methanolic sodium methylate solution. The oil remaining after evaporating in vacuo crystallizes after addition of an equimolar amount of ethanolic fumaric acid as the hydrogenfumarate of melting point 148°–149° C.

Example 38

N-(1,3-Dimorpholino-2-propyl)-1-methyl-4-imidazolesulfonamide 4 g (17.5 mmol) of 1,3-dimorpholino-2-propylamine and 3.5 g (17.5 mmol) of MSTFA [N-methyl-N-(trimethylsilyl)trifluoroacetamide] are combined under argon and stirred at room temperature for 17 hours. The clear solution is then concentrated in vacuo at 40° C./0.1 torr. A solution of 3.16 g (17.5 mmol) of 1-methyl-4-imidazolesulfonyl chloride in 20 ml of absolute dichloromethane is added at 20° C. with stirring to the oil obtained. After further stirring for 6 hours at 20° C., the solvent is distilled off in vacuo at 20° C./18 torr. The oil remaining crystallizes from isopropanol. After decolorization with active carbon, recrystallization from methanol/isopropanol gives the title compound of melting point 191°–192° C.

Yield: 3.9 g (60% of theory).

Example 39

N-(3-N-Ethyl-N-isopropylaminopropyl)-1-methyl-4-imidazolesulfonamide

A solution of 10.8 g (0.06 mol) of 1-methyl-4-imidazolesulfonyl chloride from Example C-1 is added dropwise at room temperature to a solution of 13 g (0.06 mol) of 1-trimethylsilylamino-N-ethyl-N-isopropyl-3-propylamine in 100 ml of acetonitrile and the mixture is stirred further for 6 hours. The residue remaining after evaporating in vacuo is recrystallized from isopropanol in order to give the title compound of melting point 145°–146° C.

Yield: 5.7 g (29.2% of theory).

Example 40

N-[4-(4-Hydroxyphenyl)piperazino]-5-chloro-1-methyl-4-imidazolesulfonamide

A solution of 20 g (93 mmol) of 5-chloro-1-methyl-4-imidazolesulfonyl chloride in 250 ml of chloroform is added dropwise at room temperature to 16 g (90 mmol) of 4-(4-hydroxyphenyl)piperazine in 250 ml of chloroform. 41 ml (0.3 mol) of triethylamine are then slowly added dropwise. When, after stirring for 6 hours at room temperature, acid chloride is no longer present by thin layer chromatography, the precipitate formed is filtered off, washed several times with water, dried and recrystallized from acetonitrile. The title compound melts at 249°–250° C.

Yield: 22 g (66.3% of theory).

Example 41

1-(1-Methyl-5-chloro-4-imidazolesulfonyl)4-[4-(1-methyl-5-chloro-4-imidazolesulfonyloxy)phenyl]piperazine The mother liquors from Example 40 are evaporated in vacuo. The residue is washed with water and recrystallized from water/ethanol. The title compound thus obtained melts at 196°–197° C.

Yield: 3.5 g (21.1% of theory).

Example 42

4-(1-Methyl-4-imidazolesulfonyl)tetrahydro-4H-1,4-thiazine 2 g (11 mmol) of 1-methyl-4-imidazolesulfonyl chloride from Example C-1, dissolved in 20 ml of acetonitrile, are added dropwise with stirring at room temperature to a solution of 1.51 ml (15 mmol) of thiomorpholine in 50 ml of acetonitrile. The reaction mixture is subsequently stirred for 6 hours, filtered and evaporated in vacuo. The residue remaining is recrystallized from isopropanol in order to give the title compound of melting point 154°–155° C.

Yield: 1.37 g (50% of theory).

The following are obtained in an analogous manner to that described in Example 42:

| Ex. | Name | Melting point °C. (solvent for recrystallization) |
|---|---|---|
| 43 | 1-[3-(1-methyl-5-imidazolesulfonyl)-aminopropyl]-2-pyrrolidinone from N-(3-aminopropyl)-2-pyrrolidinone and 1-methyl-4-imidazolesulfonyl chloride | 125–126 (i-PrOH) |
| 44 | N-(3-methoxypropyl)-1-methyl-4-imidazolesulfonamide from 3-methoxypropylamine (2 mol per mol acid chloride) and 1-methyl-4-imidazolesulfonyl chloride | 95–96 (i-PrOH) |
| 45 | N-(4-hydroxyphenethyl)-1-methyl-4-imidazolesulfonamide from tyramine and 1-methyl-4-imidazolesulfonyl chloride in dichloromethane instead of acetonitrile | 207–208 ($H_2O$) |
| 46 | N-(4-hydroxyphenethyl-)-5-chloro-1-methyl-4-imidazolesulfonamide from tyramine and 5-chloro-1-methyl-4-imidazolesulfonyl chloride in dichloromethane instead of acetonitrile | 170 ($H_2O$) |
| 47 | 1,6-bis(5-chloro-1-methyl-4-imidazolesulfonamido)hexane from hexamethylenediamine and 5-chloro-1-methyl-4-imidazolesulfonyl chloride | 209–210 ($H_2O$/MeOH) |
| 48 | N-(2-cyanoethyl)-1-methyl-4-imidazolesulfonamide from 3-aminopropionitrile and 1-methyl-4-imidazolesulfonyl chloride | 122–124 (EtOH) |
| 49 | N-(5-cyanopentyl)-1-methyl-4-imidazolesulfonamide from 6-aminocapronitrile and 1-methyl-4-imidazolesulfonyl chloride | 92–94 ($H_2O$) |

Example 50

N-(3-Propargyl)-1-methyl-4-imidazolesulfonamide

A solution of 3 g (16.6 mmol) of 1-methyl-4-imidazolesulfonyl chloride from Example C-1 in 40 ml of dichloromethane is added dropwise with further cooling and with stirring to an initially introduced solution, cooled to −20° C., of 1.14 ml (16.6 mmol) of propargylamine in 30 ml of dichloromethane. The reaction solution is then slowly allowed to warm to room temperature. The precipitate depositing during the course of this is filtered off with suction and recrystallized from isopropanol in order to form the title compound of melting point 145° C.

Yield: 1.5 g (45.3% of theory).

Example 51

4-[2-(1-Methyl-4-imidazolesulfonyl)aminoethyl]-phenoxyacetic acid 6.3 g (32 mmol) of 4-(2-aminoethyl)phenoxyacetic acid are added to a solution of 9.7 g (79 mmol) of potassium carbonate in 50 ml of water and the mixture is stirred for 5 minutes. A suspension of 5.8 g (32 mmol) of 1-methyl-4-imidazolesulfonyl chloride from Example C-1 in 20 ml of water is slowly added to this suspension. The mixture is heated to 80° C. and stirred at this temperature for 2 hours. After cooling to room temperature, the reaction solution is acidified to pH 4 using 2N hydrochloric acid. The precipitate deposited is separated off, washed several times with water and recrystallized from dilute acetic acid in order to give the title compound of melting point 203°-204° C.

Yield: 6 g (55.2% of theory).

Example 52

4-[2-(5-Chloro-1-methyl-4-imidazolesulfonyl)aminoethyl]phenoxyacetic acid

In an analogous manner to that described in Example 51, the title compound from 5-chloro-1-methyl-4-imidazolesulfonyl chloride and 4-(2-aminoethyl)-phenoxyacetic acid is obtained in 29% yield. The compound recrystallized from water melts at 174°-175° C.

Example 53

N-(3-Morpholino-1-propyl)-1-methyl-5-imidazolesulfonamide hydrochloride 1 g (2.8 mmol) of N-(3-morpholinopropyl)-4-chloro-1-methyl-5-imidazolesulfonamide from Example 31 is dissolved in 130 ml of 25% strength aqueous ethanol, 0.3 g of Pd/C catalyst is added and the mixture is hydrogenated with shaking at an initial pressure of 3.45 bar until absorption of hydrogen is complete. The catalyst is filtered off. The filtrate is concentrated in vacuo and the residue is recrystallized from ethanol. The title compound of melting point 205°-206° C. is obtained in a yield of 0.8 g (88% of theory).

Example 54

1,6-Bis(1-methyl-4-imidazolesulfonamido)hexane 13 g (27 mmol) of 1,6-bis(5-chloro-1-methyl-4-imidazolesulfonamido)hexane from Example 47 in 250 ml of 1N sodium hydroxide solution are hydrogenated over 3 g of 10% strength Pd/C catalyst while shaking at an initial pressure of 3.45 bar until absorption of hydrogen is complete. After separating off the catalyst, the filtrate is evaporated in vacuo. The residue was recrystallized from water/methanol in order to give the title compound as colorless crystals of melting point 153°-154° C.

Yield: 6.1 g (55% of theory).

Example 55

N-[3-(1-Piperazinyl)propyl]-1-methyl-40-imidazolesulfonamide hydrochloride 3 g (7.2 mmol) of N-[3-(4-benzyl-1-piperazinyl)-1-propyl]-1-methyl-4-imidazolesulfonamide hydrochloride from Example 26 in a solution of 30 ml of ethanol in 150 ml of 25% strength ammonium hydroxide solution are hydrogenated in the presence of 1 g of Pd/C catalyst with shaking at an initial pressure of 3.45 bar and room temperature until absorption of hydrogen is complete. After concentrating under reduced pressure, the residue is recrystallized from ethanol in order to give the desired compound of melting point 174°-175° C.

Yield: 1.4 g (59% of theory).

Example 56

4-Methyl-4-[3-(1-methyl-4-imidazolesulfamoyl)-1-propyl]morpholinium iodide 2 g (6.9 mmol) of N-(3-morpholinopropyl)-1-methyl-4-imidazolesulfonamide from Example 7 are stirred at room temperature for 8 hours in a solution of 0.48 ml (7.6 mmol) of iodomethane in 50 ml of acetonitrile. The precipitate formed is separated off, washed well with acetonitrile and dried in order to give the title compound of melting point 204°-205° C.

Yield: 2.5 g (84% theory).

Example 57

4-(1-Methyl-4-imidazolesulfonyl)tetrahydro-4H-1,4-thiazine-1,1-dioxide 1 g (4 mmol) of 4-(1-methyl-4-imidazolesulfonyl)tetrahydro-4H-1,4-thiazine from Example 42 are taken up in 10 ml of chloroform and a solution of 1.39 g (8 mmol) of m-chloroperoxybenzoic acid is added dropwise at 0°-5° C. After warming to room temperature, the mixture is subsequently stirred for 2 hours, during which the reaction product precipitates and is filtered off with suction and recrystallized from water. The title compound thus obtained melts at 179°-180° C.

Yield: 0.3 g (26.6% of theory).

Example 58

Ethyl 4-[4-(5-chloro-1-methyl-4-imidazolesulfonyl)-piperazinyl]phenoxyacetate 2 g (5.6 mmol) of N-[4-(4-hydroxyphenyl)-piperazino]-5-chloro-1-methyl-4-imidazolesulfonamide from Example 40 are taken up in 70 ml of ethanol, 0.22 g (5.5 mmol) of sodium hydroxide is added, the mixture is stirred for 30 minutes and 0.86 g (6 mmol) of ethyl bromoacetate is added dropwise. If, after stirring at room temperature for 6 hours, the reaction is still incomplete according to TLC, a further 0.42 g (2.5 mmol) of ethyl bromoacetate and 0.12 g (3 mmol) of sodium hydroxide are added, and the mixture is heated to 50° C. and subsequently stirred for about 10 hours. After evaporating in vacuo, the residue is taken up in dichloromethane and washed with 2N NaOH. The organic phase is evaporated in vacuo after drying over sodium sulfate. The crystalline residue can be recrystallized from isopropanol. The title compound thus obtained melts at 148°–149° C.

Yield: 0.8 g (32% of theory).

Example 59

N-(6-Aminohexyl)-1-methyl-4-imidazolesulfonamide dihydrochloride 2.6 g (10 mmol) of N-(5-cyanopentylamino)-1-methyl-4-imidazolesulfonamide from Example 49 are dissolved in 50 ml of about 5N ethanolic ammonia solution, 1 g of Raney nickel is added and the mixture is hydrogenated with shaking at an initial pressure of 3.45 bar until absorption of hydrogen is complete. The catalyst is filtered off. The filtrate is concentrated in vacuo. The remaining oil is dissolved in absolute ethanol. On addition of ethanolic hydrochloric acid, the title compound precipitates as a crystalline salt which, after separating off and drying, has a melting point of 215°–223° C.

Yield: 2.3 g (60% of theory).

Example 60

N-(3-Aminopropyl)-1-methyl-4-imidazolesulfonamide hydrochloride

In an analogous manner to that described in Example 59, the title compound of melting point 168°–169° C. is obtained in about 55% yield from N-(3-cyanoethylamino)-1-methyl-4-imidazolesulfonamide from Example 48.

Example 61

N-(3-Thiomorpholinopropyl)-1-methyl-4-imidazolesulfonamide S-oxide hydrochloride A solution of 3.5 g (10 mmol) of N-(3-thiomorpholinopropyl)-1-methyl-4-imidazolesulfonamide hydrochloride from Example 13 in 30 ml of 50% aqueous methanol is added dropwise at −5° C. to a solution of 1.9 g (9 mmol) of sodium iodate in 25 ml of water. A precipitate formed in the course of this goes into solution again after a further 20 minutes. After standing overnight, excess sodium bicarbonate is added to the reaction solution, which is evaporated to dryness in vacuo and purified by column chromatography on silica gel using dichloromethane:methanol 9:1 to 0:10. The eluted oil is converted into the hydrochloride using ethanolic hydrochloric acid and the title compound thus obtained is recrystallized to give a melting point of 186° C. from ethanol/methanol.

Yield: 1.2 g (32% of theory).

Example 62

N-(3-Methylamino-1-propyl)-1-methyl-4-imidazolesulfonamide hydrochloride 15 g (41.7 mmol) of N-[3-(N-benzyl-N-methylamino)-1-propyl]-1-methyl-4-imidazolesulfonamide hydrochloride from Example 28 are hydrogenated in a solution of 100 ml of 25% strength ammonia solution and 100 ml of ethanol in the presence of 2 g of 10% strength Pd/C catalyst. After completion of the absorption of hydrogen and filtering off the catalyst, the filtrate is evaporated in vacuo. The residue is recrystallized from ethanol in order to give the title compound of melting point 169°–170° C.

Yield: 2.3 g (20.5% of theory).

C) Intermediates (imidazolesulfonyl chlorides)

Example 1

1-Methyl-4-imidazolesulfonyl chloride

1-Methylimidazole (250 g, 3.05 mol) is added dropwise to chlorosulfuric acid (600 ml, 9.03 mol), in such a way that an internal temperature of 30° C. is not exceeded, without aspirating the hydrogen chloride formed. After addition is complete, the reaction mixture is stirred at 150° C. for 6 h. Thionyl chloride (340 ml, 4.66 mol) is added at 60° C. and the mixture is then heated at a bath temperature of 100° C. for 6 h. After cooling to room temperature, the viscous reaction mixture is poured onto sufficient ice such that that the end about 7.5 l of a water-ice mixture remains. The precipitate deposited is filtered off with suction and briefly sucked dry in air. It is then either dried in a thin layer in a vacuum drying oven at 50° C. and 15 torr, or it is preferably taken up using dichloromethane, dried over sodium sulfate and freed from solvent in vacuo. Yield: 176 g (32% of theory) of colorless crystals were obtained (melting point: 89°–90° C.). To remove the isomeric 5-imidazolesulfonic acid formed as a by-product from the mother liquor, the latter is largely concentrated in vacuo at 15 torr in a rotary evaporator. On addition of ethanol, an imidazolesulfonic acid mixture crystallizes out, which can be recrystallized from ethanol.

Example 2

1-Ethyl-4-imidazolesulfonyl chloride

In an analogous manner to that described in Example C-1, the title compound of melting point 34°–35° C. is obtained in about 24.7% yield from 1-ethylimidazole by means of chlorosulfonic acid and thionyl chloride.

Example 3

1,2-Dimethyl-4-imidazolesulfonyl chloride

In an analogous manner to that described in Example C-1, the title compound is obtained in 30% yield from 1,2-dimethylimidazole by means of chlorosulfonic acid and thionyl chloride. It can be recrystallized from toluene/cyclohexane and then has a melting point of 90°–91° C.

Example 4

1-Propyl-4-imidazolesulfonyl chloride and 1-propyl-5-imidazolesulfonyl chloride

In an analogous manner to that described in Example C-1, a mixture of the title compound is obtained in about 57% yield from 1-propylimidazole by means of chlorosulfonic acid and thionyl chloride, which mixture is expediently separated in the form of their derivatives.

Example 5

1-Butyl-4-imidazolesulfonyl chloride and 1-butyl-5-imidazolesulfonyl chloride

In an analogous manner to that described in Example C-1, a mixture of the title compounds is obtained in about 17% yield from 1-butylimidazole by means of chlorosulfonic acid and thionyl chloride, which mixture is expediently separated in the form of their derivatives.

The compounds of the formula I as in the examples from sections A and B are collated in the following Table 1; if the salts were prepared in the examples, this is also taken into account in the table. The process variants by which the compounds in the examples concerned were prepared are furthermore also indicated in the table.
TABLE 1
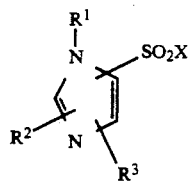
(I)
| Ex. | Proc. var. | $R^1$ | $R^2$ | $R^3$ | Position of the $SO_2X$ group | X |
|---|---|---|---|---|---|---|
| A)1 | a | $CH_3$ | Cl | H | 4 (5-position) | OH |
| 2 | c | $C_2H_5$ | H | " | " | " |
| 3 | c | $CH_3$ | " | " | " | " |
| 4 | c,d | " | " | " | 2 | " |
| 5 | c | " | Cl | " | 5 (4-Position) | " |
| 6 | b | " | H | " | " | " |
| B)7 | e | " | " | " | 4 | 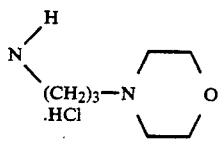 |
| 8 | f | " | " | " | " | " |
| 9 | e | " | " | " | " | 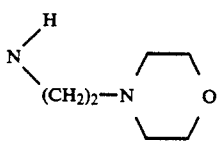 |
| 10 | e | " | " | " | " | 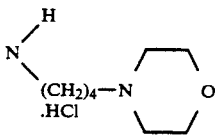 |
| 11 | e | " | " | " | " | 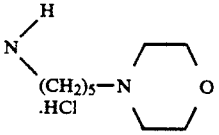 |
| 12 | e | $CH_3$ | H | H | 4 | 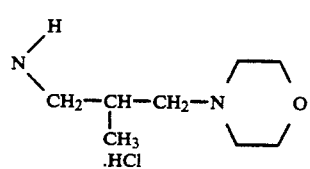 |
| 13 | e | " | " | " | " | 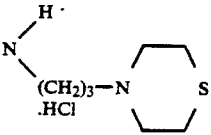 |
| 14 | e | " | " | " | " | 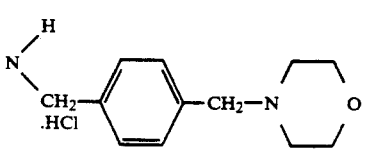 |

TABLE 1-continued structure (I): pyrimidine ring with R¹ on N, R² on C, R³ on N, SO₂X substituent

| Ex. | Proc. var. | R¹ | R² | R³ | Position of the SO₂X group | X |
|---|---|---|---|---|---|---|
| 15 | e | " | " | " | " | –NH(C₄H₉)–(CH₂)₃–N(morpholine) · HCl |
| 16 | e | " | " | " | " | –NH–(CH₂)₂–N(piperidine) · HCl |
| 17 | e | " | " | " | " | –NH–(CH₂)₃–N(2-methylpiperidine) · HCl |
| 18 | e | " | " | " | " | –NH–(CH₂)₅–N(piperidine) · HCl |
| 19 | e | CH₃ | H | H | 4 | –NH–(CH₂)₄–N(1,4-dioxa-8-azaspiro[4.5]decane) · HCl |
| 20 | e | " | " | " | " | –NH–(CH₂)₂–N(pyrrolidine) · HCl |
| 21 | e | " | " | " | " | –NH–(CH₂)₂–(1-methylpyrrolidin-2-yl) · HCl |
| 22 | e | " | " | " | " | –NH–(CH₂)₃–N(CH₃)₂ · HCl |
| 23 | e | " | " | " | " | –NH–(CH₂)₃–N(CH₂CH₂OCH₃)₂ · HCl |

TABLE 1-continued $$\text{(I)}$$

Structure: pyrimidine ring with $R^1$ on N, $SO_2X$ substituent, $R^2$ and $R^3$ positions.

| Ex. | Proc. var. | $R^1$ | $R^2$ | $R^3$ | Position of the $SO_2X$ group | X |
|---|---|---|---|---|---|---|
| 24 | e | " | " | " | " | $\text{HN–(CH}_2)_3\text{–N(CH}_2\text{C}_6\text{H}_5)_2$ |
| 25 | e | " | " | " | " | piperazinyl-phenyl-OH (N–⟨piperazine⟩–⟨C$_6$H$_4$⟩–OH) |
| 26 | e | " | " | " | -" | $\text{HN–(CH}_2)_3\text{–N⟨piperazine⟩N–CH}_2\text{–C}_6\text{H}_5$ · HCl |
| 27 | e | $CH_3$ | H | H | 4 | $\text{HN–(CH}_2)_3\text{–N⟨piperazine⟩N–CH}_3$ · 2 HOOC–CH=CH–COOH |
| 28 | e | " | " | " | " | $\text{HN–(CH}_2)_3\text{–N(CH}_3)\text{–CH}_2\text{–C}_6\text{H}_5$ · HOOC–CH=CH–COOH |
| 29 | e | " | " | " | 2 | $\text{HN–(CH}_2)_3\text{–N⟨morpholine⟩}$ · HCl |
| 30 | e | " | " | " | " | $\text{HN–(CH}_2)_2\text{–N⟨morpholine⟩}$ · HCl |
| 31 | e | " | Cl | " | 5 | $\text{HN–(CH}_2)_3\text{–N⟨morpholine⟩}$ |
| 32 | e | " | Cl | " | 4 (4-Position) | $\text{HN–(CH}_2)_3\text{–N⟨morpholine⟩}$ · HCl |

(5-position)

TABLE 1-continued $$\text{(I)}$$

Structure: pyrazine ring with $R^1$ on N, $R^2$ on C, $R^3$ on C, and $SO_2X$ substituent.

| Ex. | Proc. var. | $R^1$ | $R^2$ | $R^3$ | Position of the SO$_2$X group | X |
|---|---|---|---|---|---|---|
| 33 | e | " | CH$_3$ | " | " (2-position) | " |
| 34 | e | CH$_3$ | Cl | H | 4 | 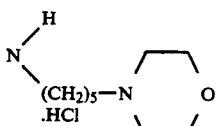 $N(H)$—(CH$_2$)$_5$—N(morpholine) · HCl |
| 35 | e | C$_3$H$_7$ | H | " | (5-position) " | 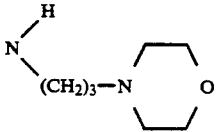 $N(H)$—(CH$_2$)$_3$—N(morpholine) |
|   | + | " | " | " | 5 | 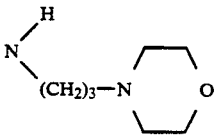 $N(H)$—(CH$_2$)$_3$—N(morpholine) |
| 36 | e | C$_4$H$_9$ | " | " | 4 | 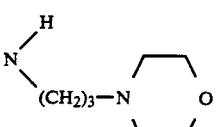 $N(H)$—(CH$_2$)$_3$—N(morpholine) |
|   | + | " | " | " | 5 | 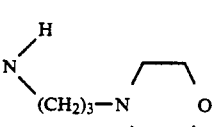 $N(H)$—(CH$_2$)$_3$—N(morpholine) |
| 37 | e | C$_2$H$_5$ | " | " | 4 | 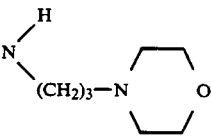 $N(H)$—(CH$_2$)$_3$—N(morpholine) · HOOC—CH=CH—COOH |
| 38 | g | CH$_3$ | " | " | " | 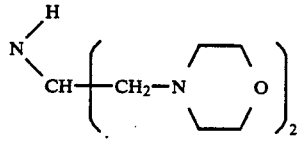 $N(H)$—[CH(—CH$_2$—N(morpholine))]$_2$ |
| 39 | g | " | " | " | " | 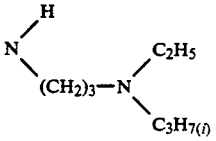 $N(H)$—(CH$_2$)$_3$—N(C$_2$H$_5$)(C$_3$H$_{7(i)}$) |
| 40 | e | " | " | " | " | 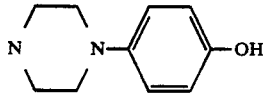 piperazinyl-C$_6$H$_4$—OH |

TABLE 1-continued

Structure (I): pyrazine ring with R¹ on N, R² on adjacent C, R³ on C, and SO₂X substituent.

| Ex. | Proc. var. | R¹ | R² | R³ | Position of the SO₂X group | X |
|---|---|---|---|---|---|---|
| 41 | m | " | Cl | " | " | piperazinyl-phenyl-OSO₂-(1-methyl-5-chloroimidazol-4-yl) |
| 42 | e | " | H | " | (5-position) | thiomorpholino (N,S-ring) |
| 43 | e | " | " | " | 5 | NH—(CH₂)₃—N(2-oxopyrrolidinyl) |
| 44 | e | " | " | " | 4 | NH—(CH₂)₃—OCH₃ |
| 45 | e | " | " | " | " | NH—(CH₂)₂—C₆H₄—OH (para) |
| 46 | e | " | Cl | " | " | " |
| 47 | e | " | " | " | (5-position) | NH—(CH₂)₆—NHSO₂-(1-methyl-5-chloroimidazol-4-yl) |
| 48 | e | " | H | " | " | NH—(CH₂)₂—CN |
| 49 | e | " | " | " | " | NH—(CH₂)₅—CN |
| 50 | e | " | " | " | " | NH—CH₂—C≡CH |
| 51 | e | " | " | " | " | NH—(CH₂)₂—C₆H₄—OCH₂—COOH (para) |

TABLE 1-continued
| Ex. | Proc. var. | R¹ | R² | R³ | Position of the SO₂X group | X |
|---|---|---|---|---|---|---|
| 52 | e | " | Cl | " | " | " |
| 53 | f | " | H | " | (5-position) 5 | 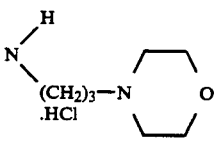 |
| 54 | f | " | " | " | 4 | 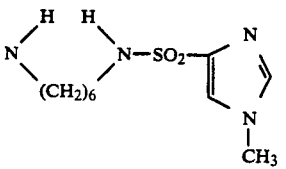 |
| 55 | h | " | " | " | " | 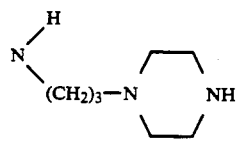 |
| 56 | j | " | " | " | " | 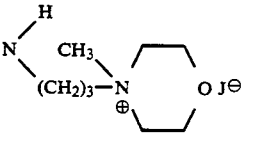 |
| 57 | k | " | " | " | " | 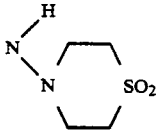 |
| 58 | l | " | Cl | " | " | 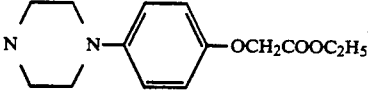 |
| 59 | i | " | H | " | (5-position) " | 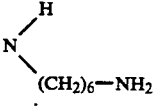 |
| 60 | i | " | " | " | " | 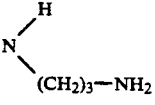 |
| 61 | k | " | " | " | " | 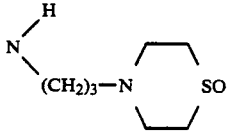 |

TABLE 1-continued

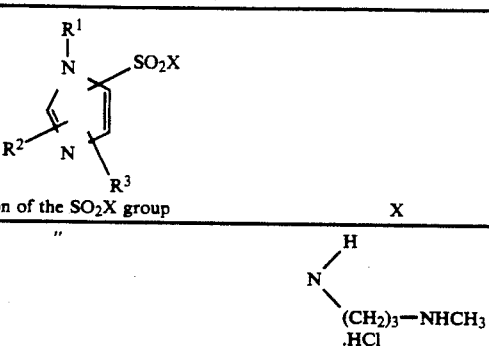

| Ex. | Proc. var. | R¹ | R² | R³ | Position of the SO₂X group | X |
|---|---|---|---|---|---|---|
| 62 | h | " | " | " | " | $\begin{array}{c}H\\ \diagup\\ N\\ \diagdown\\ (CH_2)_3-NHCH_3\\ \cdot HCl\end{array}$ |

PHARMACOLOGICAL TESTING AND RESULTS

1) Effect on the Contractility of the Skeletal Muscle After Chronic Ischemia In recent years, a marked change has taken place in ideas about the pathophysiology of chronic peripheral arterial occlusive disease as scientific interest has to an increasing extent shifted from the macrocirculation to the microcirculation. Disturbances in the microcirculation therefore manifest themselves in an undersupply of substrates with tissue ischemia resulting therefrom which, in turn, leads to an impairment in the function of the extremity concerned. The logical consequence of this is that the target organ skeletal muscle comes more and more into the forefront. This means that the therapeutic aim of any medicinal treatment has to be the improvement or—in the ideal case—the re-establishment of the normal capacity. The clinical activity is in fact also consistently determined in humans with the aid of the painless walking distance on the moving walkway.

The testing of the compounds according to the invention for their function-improving effect was therefore carried out by measurements of the contractility in the ischemic skeletal muscle using the experimental procedure described below, the standard therapeutic pentoxyfylline being additionally included in the investigations as a comparison preparation (see also Okyayuz-Baklouti, I., in: Muscle Ischaemia, Functional and Metabolic Aspects, eds I. Okyayuz-Baklouti and O. Hudlicka, Dr. C. Wolf und Sohn, Munich, pp. 103–126, 1988; Okyayuz-Baklouti, I., European J. of Pharmacology 166: 75–86, 1989).

Male Wistar rats having a body weight of 380 to 410 g were used as experimental animals. Under hexobarbital anesthesia (®Evipan—sodium, 200 mg/kg BW (=body weight) i.p.), a unilateral ligature of the right femoral artery was applied to the animals in the groin. After sprinkling penicillin sulfonamide powder for antibiotic wound care, the small operation wound was closed and the animals were continuously observed until they were completely awake. One week later, the administration of substance began by oral administration using a stomach tube (6 mg/kg BW, carboxymethylcellulose-sodium suspension) and was continued for 7 days (single administration per day, about 7h30 to 8h30). The contractility was measured 24 h after the last administration of substance in order to exclude acute effects, to be precise by the following experimental protocol:

The animals were anesthetized with ®Nembutal (pentobarbital—sodium, 35 mg/kg BW i.p.), the muscles of the extremity concerned were exposed (gastrocnemius-plantaris-soleus group) and the tendon was tied to a pressure transducer (Rhema Z6, Rhema, Hofheim) having a preload of 50 g. Superfusion with physiological saline solution (37° C.) was used to avoid drying out and cooling. The mean arterial blood pressure was recorded continuously via Statham (=blood pressure measuring device) by means of a cannulated caroted artery to control the physiological status of the animals during the experiment. All animals breathed spontaneously by means of an inserted tracheal tube.

After these preparations, the muscle was made to contract (Stimulator I, Hugo Sachs, Federal Republic of Germany) by direct electrical stimulation (2.5 mA, 2 Hz). The absolute contractility in grams at various times of stimulation was used as the measured parameter. The initial contractility of the chronic-ischemic skeletal muscle only differs insignificantly in this case (scatter of the experiments) from that of the normal muscle. Since, however, the undersupplied muscle tires more rapidly, the contractility falls during the stimulation interval of 5 minutes chosen here significantly more rapidly and strongly than in the normal non-ischemic muscle. If the maximum contractility at the start of stimulation is now divided by the residual force remaining after 5 minutes' tiring stimulation, a "tiring index TI" for the muscle concerned can be calculated; the ability to tire here is larger the larger TI is numerically. Thus, the TI for the normal muscle treated only with the vehicle varies, depending on the experiment, between 1.78 and 3.29 (see Table 2). The ability to tire of the ischemic muscle is around 40 to 60% higher.

In Table 2, the TI of the normal muscle was compared with the TI of the ischemic treated muscle as this, most clearly, reflects a possible improvement of the function in the direction of normalization. This means that the smaller the numerical value of the percentage change, the more effective is the respective preparation, i.e. a percentage change having, for example, a negative sign means an even lower ability to tire in comparison to the non-ischemic untreated muscle. 4 to 6 individual experiments were carried out for each test preparation.

2) Antithrombotic Activity

An important factor in the genesis and the course of peripheral arterial occlusive diseases and other indications claimed for this substance group are thrombotic events. Thus, the compounds according to the invention were tested for inhibition of laser-induced thrombosis (cf. for this: Seiffge, D. and Kremer, E., Thromb. Res. 42, 331-341, 1986):

These investigations were carried out on female Sprague-Dawley rats having a body weight of about 200 g. The animals were premedicated with 0.1 mg of atropine sulfate s.c. and anesthetized with 100 mg of ketamine hydrochloride and 4 mg of xylazine per kg BW i.p. Arteriole and venules of the mesentery covered with a layer of degassed paraffin oil and having a diameter of about 13 lm were used for the investigation. The beam of a 4 W argon laser (Spectra-Physics, Darmstadt) was brought coaxially into the inverted beam of a microscope (ICM 405, LD ®Epiplan 40/0.60, Zeiss, Oberkochen) by means of a beam-adapting and adjusting unit. The wavelength used was 514.5 nm with a power above the objective of 30 mW. The exposure time per individual pulse lasted 1/15 sec. All measuring operations were recorded by video camera (®Trinicon tubes, Sony, Cologne) and stored on a recorder (®Sony U-matics ¾"). The test substances were administered orally to the experimental animals in various dosages one hour, on i.v. administration 10 min, before starting the experiment; control animals received the same amount of placebo. The substances were administered as a single administration once during the day or once during the day over the course of several days. For evaluation, the number of laser pulses which are needed in order to produce a thrombosis on the wall of a minimum size of half the vessel diameter were counted. This means the larger the number of laser pulses the more effective are the preparations in this test. The percentage inhibition of thrombosis is indicated in Table 3.

3) Acute Toxicity

The determination of the LD50 ranges was carried out in standard fashion by means of the mortality occurring in the course of 7 days in NMRI mice after single intravenous (i.v.) or intraperitoneal (i.p.) administration (NMRI=NIH Medical Research Institute). The values are likewise summarized in Table 3.

4) Additional Special Tests

The clear superiority of the compounds according to the invention, in particular compared to the preparation most frequently employed therapeutically for the treatment of peripheral circulatory disturbances, pentoxyfylline, could also be confirmed impressively in other special tests.

An important advantage of the substances according to the invention, for example the compound from Example 7, is that they inhibit thrombosis in hyperlipidemic, spontaneously hypertensive and, thus, stroke-prone rats and in atherosclerotic rabbits. Thus, the substance from Example 7 inhibits the laser-induced thrombosis after daily administration of 10 or 30 mg/kg for 7 days in hyperlipidemic hypertensive rats by 18 or 32% respectively and in atherosclerotic rabbits after daily administration of 30 mg/kg for 14 days by 36%.

Furthermore, the substances according to the invention not only inhibit laser-induced thrombus formation, but moreover they, particularly the substance of Example 7, also inhibit photochemically-induced thrombosis. In this model, rats were anesthetized as described above under 2). The investigations were carried out on mesenterial arterioles having a diameter of 11 to 50 lm. A thrombosis was induced in a modification in accordance with a method known from the literature (Herrmann, K. H. Microvasc. Res. 26, 238-249, 1983) and is based on the photochemical release of singlet oxygen, which leads locally to an endothelial lesion. The animals to be investigated received an intravenous injection of 0.3 ml of a 10% strength solution of fluorescein in isothiocyanate—Dextran 70 (FITC—Dextran 70 s, Sigma, Munich). The arterole was looked for under the microscope and centered in the observation field. The FITC—Dextran in the blood vessel was then excited using a special lamp and filter device (excitation 490 nm, emission 510 nm). For evaluation of thrombus formation, the time was taken which extended from the point of excitation to the formation of a first thrombus on the wall. 5 vessels in each animal were examined in this manner. It emerged that the thrombosis was inhibited in a dose-dependent and statistically significant manner by the compound from Example 7 (1, 3, 10 mg/kg p.o.: 69, 75, 130%). In comparison thereto, pentoxyfylline only caused an inhibition of 29, 18 and 68% at 1, 3 and 10 mg/kg p.o. After i.v. administration of 3 or 10 mg/kg of the compound from Example 7, the thrombosis was inhibited by 36% or 56% respectively; and on i.v. administration of 3 or 10 mg/kg of pentoxyfylline by 3% or 38% respectively.

Using laser-Doppler flow measurements (LDF), the erythrocyte flux (the number of cells flowing past under the laser beam x their velocity) can be measured in a noninvasive and continuous manner in the capillary bed of the skeletal muscle of the rat (perimed PF2 laser-Doppler flowmeter, Perimed, Sweden). However, this technique does not indicate absolute values of the circulation but qualitative changes in volts, where, however, the signal obtained correlates linearly with the flux. The apparatus was set as follows: 12 kHz, gain 10, time constant 1.5 sec, 37° C. The right femoral artery of male Wistar rats having a body weight of 380-430 g was exposed and the skin and the connective tissue was dissected away over a small muscle area (anterior tibia). The probe was placed about 1 mm above this area. As soon as the curve had stabilized, the femoral artery was occluded with the aid of a clamp, whereupon the LD curve in the muscle supplied by this vessel fell rapidly then, as a result of the spontaneous opening of collateral vessels, rose again slightly and finally settled down to a strongly reduced level compared to the starting value (residual circulation in the acutely ischemic muscle about 25%). At this point, the test substances were infused intravenously in aqueous solution (0.03 and 0.6 mg/kg/min). The maximum percentage increase in the erythrocyte flux after administration of substance during the occlusion (see also Okyayuz-Baklouti, I., European J. of Pharmacology, 166: 75-86, 1989) was used as the measuring parameter for the substance activity. It emerged in this case that the circulation in the microcirculation, for example after infusion of the compound from Example 7, increased in a strong and dose-dependent manner (+53.3% at the lower and +80.6% at the higher dosage). In comparison thereto, pentoxyfylline caused an increase by 24.6% at the low and by 33.1% at the higher dosage. 3-7 animals were employed per preparation and dose.

The contractility in the acutely ischemic muscle was measured in a similar experimental procedure, as described under 1). The muscle, initially normally supplied with blood, was made to contract isometrically by direct electrical stimulation (1.2 Hz, 2.5 mA). The right femoral artery was then occluded for 5 min by means of a clamp. The contractility significantly decreases in this case owing to the insufficient supply of substrate (infusion of the vehicle). The vessel was then reopened and the starting contractility before the first occlusion was attained. During the second occlusion which then followed, the preparations to be tested were administered intravenously in aqueous solution via the jugular vein. 4-8 animals were employed per preparation and dose. The decrease in the contractility during occlusion with and without substance administration was compared and the percentage change was used to evaluate the substance activity. The substances according to the invention, for example the compound of Example 7, were also remarkable in this test for outstanding effects. Thus, the contractility after a dose of 0.03 mg/kg/min was improved by +17.2%, and after a dose of 0.3 mg/kg/min by +25.2%, while pentoxyfylline also only showed marginal activity in this functional test.

Thus, the compounds according to the invention have outstanding activities on the capacity of the ischemic muscle both during chronic and during acute inadequate circulation, and also favorable effects on capillary circulation coupled with an excellent inhibition of intravascular thrombosis.

TABLE 2

| TIRING INDEX (TI) SKELETAL MUSCLE OF THE RAT | | | |
|---|---|---|---|
| Compound from Example | TI of normal non-treated muscle | TI of ischemic treated muscle | Percentage change |
| 1 | 2.23 | 2.26 | +1.3 |
| 3 | 2.11 | 2.26 | +7.1 |
| 7/8 | 2.78 | 2.79 | +0.3 |
| 9 | 2.24 | 2.47 | 10.3 |
| 10 | 2.27 | 2.19 | −3.6 |
| 11 | 2.05 | 2.52 | +22.9 |
| 13 | 3.29 | 2.95 | −10.1 |
| 14 | 2.27 | 2.57 | +13.4 |
| 15 | 1.77 | 1.96 | +10.9 |
| 17 | 2.38 | 2.04 | −14.3 |
| 19 | 1.98 | 2.20 | +11.1 |
| 20 | 2.08 | 2.56 | +23.1 |
| 21 | 1.96 | 2.34 | +19.4 |
| 23 | 1.77 | 2.18 | +23.1 |
| 25 | 1.98 | 2.11 | +6.6 |
| 26 | 1.98 | 2.49 | +25.7 |
| 27 | 1.96 | 2.6 | +32.6 |
| 28 | 1.98 | 2.27 | +14.6 |
| 29 | 1.98 | 2.74 | +38.4 |
| 30 | 3.29 | 2.82 | −14.2 |
| 32 | 2.36 | 2.51 | +6.4 |
| 33 | 2.05 | 2.30 | +12.2 |
| 34 | 1.98 | 1.98 | +0.0 |
| 37 | 2.27 | 2.09 | −7.9 |
| 38 | 1.98 | 2.18 | +10.1 |
| 40 | 2.36 | 3.18 | +34.7 |
| 41 | 1.84 | 2.18 | +18.5 |
| 42 | 2.28 | 2.84 | +24.6 |
| 43 | 1.77 | 2.29 | +29.4 |
| 45 | 1.84 | 2.14 | +16.3 |
| 46 | 2.19 | 2.05 | −6.4 |
| 47 | 2.32 | 2.46 | +6.0 |
| 51 | 2.36 | 2.92 | +23.7 |
| 52 | 1.84 | 2.16 | +17.4 |
| 53 | 3.29 | 3.18 | −3.3 |
| 54 | 1.85 | 2.55 | +37.8 |
| 58 | 2.11 | 2.07 | −1.9 |
| 62 | 1.96 | 2.5 | +27.8 |
| Pentoxyfylline | 2.23 | 3.20 | +43.5 |

For all preparations 6 mg/kg p.o. over 7 days, n = 4 − 6.

TABLE 3

| INHIBITION OF LASER-INDUCED THROMBOSIS IN MESENTERIAL ARTERIOLES OF THE RAT AND TOXICITY | | | |
|---|---|---|---|
| Compound | Dose (mg/kg p.o.) | Percentage change vs control | Toxicity (LD$_{50}$ range) mg/kg |
| 1 | 10 | 13 | >200 i.v. |
| 3 | 20 | 23 | |
| 7/8 | 10 | 36 | >100 i.v. |
| 10 | 10 | 38 | >100 i.v. |
| 12 | 20 | 24 | >100 i.v. |
| 13 | 20 | 14 | |
| 14 | 20 | 13 | >100 i.v. |
| 21 | 20 | 24 | |
| 25 | 10 | 22 | >300 i.p. |
| 26 | 10 | 24 | |
| 27 | 20 | 23 | >100 i.v. |
| 29 | 10 | 21 | >100 i.v. |
| 30 | 10 | 45 | >100 i.v. |
| 32 | 10 | 21 | >200 i.v. |
| 33 | 10 | 18 | |
| 34 | 10 | 15 | >100 i.v. |
| 38 | 10 | 21 | |
| 40 | 10 | 17 | >1200 i.p. |
| 43 | 20 | 15 | |
| 46 | 10 | 29 | >1200 i.p. |
| 46 | 30 | 29 | |
| 53 | 10 | 18 | >100 i.v. |
| 54 | 10 | 17 | >1200 i.p. |
| 56 | 10 | 24 | >100 i.v. |
| 57 | 10 | 19 | |

We claim:

1. An imidazole compound of the formula I

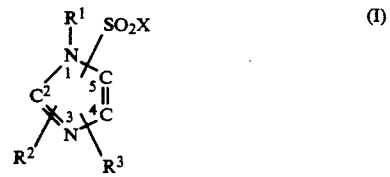

in which
$R^1$ is $(C_1-C_6)$-alkyl,
$R^2$ and $R^3$ are identical or different and in each case are H, halogen, or $(C_1-C_3)$-alkyl,
X is an amino group of the formula II

in which
$R^4$ is H, or $(C_1-C_7)$-alkyl or said $(C_1-C_7)$-alkyl substituted by CN, NH$_2$ or COOH,
$R^5$ is $(C_1-C_8)$-alkyl in which, when it contains more than 1 carbon atom, there can also be a phenylene radical between 2 carbon atoms and in which the aliphatic carbon atoms are substituted by 1 or more of a heterocyclic radical selected from the group consisting of morpholino, thiomorpholino and piperazino, or said heterocyclic radical substituted by one or more of:
$(C_1-C_3)$-alkyl,
phenyl,
phenylalkyl having 1-3 carbon atoms in the alkyl moiety, OH or oxo, including the open and cyclic ketal forms having 2-6 carbon atoms in the ketal moiety, and in which the ring sulfur atom, when present, can also be oxidized to the sulfoxide or sulfone form, or in which $R^4$ and $R^5$, together with the nitrogen atom to which they are bonded, form a heterocyclic ring selected from the group consisting of morpholino, thiomorpholino and piperazino, with the exception of the unsubstituted morpholine ring

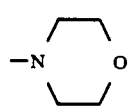

and in which the heterocyclic ring can otherwise be substituted by the following groups:
($C_1$–$C_3$)-alkoxy,
phenylalkyl having 1–4 carbon atoms in the alkyl moiety,
phenyl or phenyl substituted by 1 or more of the groups:
($C_1$–$C_3$)-alkyl,
OH,
($C_1$–$C_3$)-alkoxy,
($C_1$–$C_3$)-alkoxy-COOH,
($C_1$–$C_3$)-alkoxy-COO($C_1$–$C_4$)alkyl,

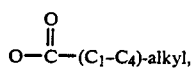

O—SO$_2$—C$_6$H$_5$,
O—SO$_2$—C$_6$H$_4$CH$_3$,
a radical of the formula

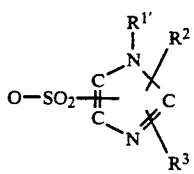

in which $R^{1'}$ is ($C_1$–$C_6$)-alkyl or H, and $R^2$ and $R^3$ are identical or different and in each case are H, halogen or ($C_1$–$C_3$)-alkyl,
and the ring sulfur atom, when present, can also be oxidized to the sulfoxide or sulfone form,
or a physiologically tolerable salt thereof.

2. An imidazole compound as claimed in claim 1, wherein in formula I at least one of the following features are present:
a) $R^1$ is CH$_3$ or C$_2$H$_5$,
b) $R^2$ and $R^3$ are identical or different and in each case are H, CL or CH$_3$ and
c) the —SO$_2$X radical is attached to the carbon atom in the 2- or 4-position of the imidazole ring.

3. An imidazole compound of the formula I as claimed in claim 1, wherein X is an amino group of the formula II $$-N\begin{matrix}R^4\\R^5\end{matrix} \quad (II)$$

where $R^4$ is H and
$R^5$ is a (C$_2$–C$_5$)-alkyl radical or said (C$_2$–C$_5$)-alkyl radical in which there is a phenylene radical between 2 carbon atoms and its aliphatic carbon atoms are substituted by a total of 1 or 2 of a monocyclic 6-membered saturated heterocyclic radical which is

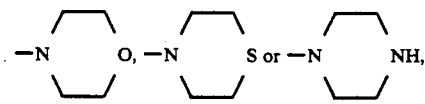

the latter of which is unsubstituted or is substituted by CH$_3$ or benzyl, or in which
$R^4$ and $R^5$, together with the nitrogen atom to which they are bonded, form a saturated 6-membered heterocyclic ring which is

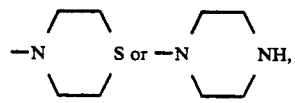

the latter of which is unsubstituted or is substituted by one of the following radicals

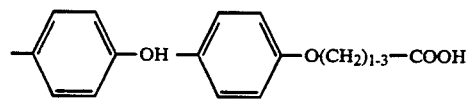

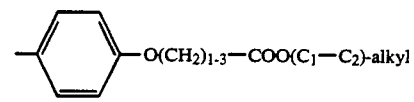

or

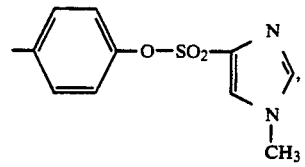

or a physiologically tolerable salt thereof.

4. N-(2-morpholinoethyl)-1-methyl-2-imidazolesulfonamide, which is the compound of the formula I as claimed in claim 1 in which
$R^1$ is CH$_3$,
$R^2$ and $R^3$ are H,
the SO$_2$X group is attached to the carbon atom in the 2-position and

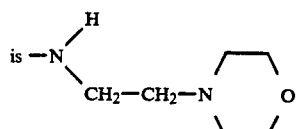

or a physiologically tolerable salt thereof.

5. N-(3-morpholinopropyl)-1-methyl-4-imidazolesulfonamide, which is the compound of the formula I as claimed in claim 1 in which
$R^1$ is CH$_3$, $R^2$ and $R^3$ are H, the $SO_2X$ group is attached to the carbon atom in the 4-position and

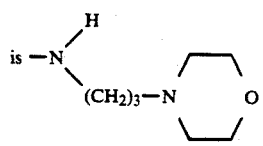

or a physiologically tolerable salt thereof.

6. An imidazole compound of the formula I as claimed in claim 1 wherein $R^5$ is morpholine, thiomorpholine or piperazine.

7. An imidazole compound of the formula I as claimed in claim 1 wherein $R^4$ and $R^5$, together with the amide nitrogen to which they are bonded, form a thiomorpholine or piperazine ring.

8. A pharmaceutical composition for the prophylaxis or treatment of circulatory disturbances and of the disorders resulting therefrom, which comprises an effective amount of at least one compound of the formula I as claimed in claim 1 or at least one physiologically tolerable salt together with a physiologically acceptable excipient.

9. The pharmaceutical composition as claimed in claim 8 for the prophylaxis or treatment of disturbances of the microcirculation.

10. A method for the prophylaxis or treatment of circulatory disturbances and of the disorders resulting therefrom, which comprises administering to a host a pharmaceutical composition as claimed in claim 8.

11. A method for the prophylaxis or treatment of circulatory disturbances and of the disorders resulting therefrom, which comprises administering to a host an effective amount of a compound of the formula I as claimed in claim 1.

* * * * *

UNITED STATES PATENT AND TRADEMARK OFFICE
CERTIFICATE OF CORRECTION

PATENT NO. : 5,232,922
DATED : August 03, 1993
INVENTOR(S) : Dr. Rolf Graeve et al.

It is certified that error appears in the above-indentified patent and that said Letters Patent is hereby corrected as shown below:

Claim 4, column 44, line 56, insert --X-- after "and".

Claim 5, column 45, line 3, insert --X-- after "and".

Signed and Sealed this

Twenty-first Day of June, 1994

Attest:

BRUCE LEHMAN

*Attesting Officer*      *Commissioner of Patents and Trademarks*